United States Patent
Mueller et al.

(10) Patent No.: US 9,034,307 B2
(45) Date of Patent: *May 19, 2015

(54) AGENT FOR FIBERS CONTAINING KERATIN, CONTAINING AT LEAST ONE SPECIFIC AMPHIPHILIC CATIONIC POLYMER AND AT LEAST ONE ADDITIONAL FILM-FORMING CATIONIC AND/OR STABILIZING POLYMER

(71) Applicant: Henkel AG & Co. KGaA, Dusseldorf (DE)

(72) Inventors: Burkhard Mueller, Hamburg (DE); Pamela Kaftan, Hamburg (DE)

(73) Assignee: HENKEL AG & CO. KGAA, Dusseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/941,169

(22) Filed: Jul. 12, 2013

(65) Prior Publication Data
US 2013/0295034 A1 Nov. 7, 2013

Related U.S. Application Data

(63) Continuation of application No. 13/028,267, filed on Feb. 16, 2011, now Pat. No. 8,506,941.

(30) Foreign Application Priority Data

Aug. 18, 2008 (DE) .......................... 10 2008 038 109
Nov. 28, 2008 (DE) .......................... 10 2008 059 479
Jul. 21, 2009 (WO) ................. PCT/EP2009/059350

(51) Int. Cl.
*A61K 8/81* (2006.01)
*A61Q 5/06* (2006.01)
*A61K 8/73* (2006.01)

(52) U.S. Cl.
CPC .............. *A61K 8/8182* (2013.01); *A61K 8/731* (2013.01); *A61K 2800/5426* (2013.01); *A61K 2800/594* (2013.01); *A61Q 5/06* (2013.01); *A61K 8/817* (2013.01)

(58) Field of Classification Search
CPC ..... A61K 8/731; A61K 8/8162; A61K 8/817; A61K 2800/594; A61K 2800/5426; A61Q 5/06
See application file for complete search history.

(56) References Cited

U.S. PATENT DOCUMENTS

| 3,753,968 | A | 8/1973 | Ward |
|---|---|---|---|
| 6,235,913 | B1 | 5/2001 | Raths et al. |
| 6,383,477 | B1 | 5/2002 | Lede et al. |
| 6,852,815 | B1 | 2/2005 | Chuang et al. |
| 7,332,466 | B2 | 2/2008 | Schmid et al. |
| 2006/0013785 | A1 | 1/2006 | Lauscher et al. |
| 2006/0257344 | A1* | 11/2006 | Nguyen et al. ............... 424/70.7 |
| 2009/0236251 | A1 | 9/2009 | Berdelle-Hilge et al. |

FOREIGN PATENT DOCUMENTS

| AU | 730455 | B2 | 5/2000 |
|---|---|---|---|
| DE | 3139438 | A1 | 4/1983 |
| DE | 19756454 | C1 | 6/1999 |
| DE | 19937434 | A1 | 7/2000 |
| DE | 10240757 | A1 | 7/2003 |
| DE | 102006005451 | A1 | 8/2007 |
| EP | 1800659 | A1 | 6/2007 |

OTHER PUBLICATIONS

"Aquastyle 300." ISP Corporation, Dec. 6, 2006, Retrieved from http://www.ispjapan.co.jp/pc_refguide/pdf/AquaStyle_300_jp, pp. 71, 84-94, on Dec. 3, 2009.

Rigoletto, Raymond et al., "Polyquartenium-69: A New Fixative Polymer with Enhanced Styling Benefits," Cosmetic Science Technology, Jan. 1, 2007, p. 142.

International Cosmetic Ingredient Dictionary & Handbook. The Cosmetic Toiletry and Fragrance Association, 7th Edition, 1997.

* cited by examiner

*Primary Examiner* — Gina Justice
*Assistant Examiner* — Genevieve S Alley
(74) *Attorney, Agent, or Firm* — Ingrassia Fisher & Lorenz, P.C.

(57) ABSTRACT

Agent for treating fibers containing keratin, particularly human hair, comprising, in a cosmetically acceptable carrier: (a) at least one amphiphilic, cationic polymer having at least one structural unit of formulae (I) to (IV), wherein; $R^1$ and $R^4$ are independently hydrogen or a methyl group, $X^1$ and $X^2$ are independently oxygen or an NH group, $A^1$ and $A^2$ are independently an ethane-1,2-diyl, propane-1,3-diyl or butane-1,4-diyl group, $R^2$, $R^3$, $R^5$ and $R^6$ are independently a ($C_1$ to $C_4$)-alkyl group, $R^7$ is a $C_8$ to $C_{30}$)-alkyl group and; (b) at least one film-forming cationic and/or stabilizing cationic polymer. The invention also relates to use of agents for temporarily styling hair and for haircare, particularly as an aerosol hairspray or mousse.

10 Claims, No Drawings

AGENT FOR FIBERS CONTAINING KERATIN, CONTAINING AT LEAST ONE SPECIFIC AMPHIPHILIC CATIONIC POLYMER AND AT LEAST ONE ADDITIONAL FILM-FORMING CATIONIC AND/OR STABILIZING POLYMER

CROSS REFERENCE TO RELATED APPLICATIONS

The present application is a continuation of U.S. patent application Ser. No. 13/028,267, filed on Feb. 16, 2011, which itself is a continuation of International Patent Application No. PCT/EP2009/059350 filed 21 Jul. 2009, which claims priority to German Patent Application Nos. 10 2008 038 109.8 filed 18 Aug. 2008 and 10 2008 059 479.2 filed 28 Nov. 2008, each of which are incorporated herein by reference.

The present invention relates to agents for treating hair containing a combination of at least one specific amphiphilic, cationic polymer with at least one film-forming cationic and/or setting polymer, use of these agents for temporary shaping and/or care of keratin-containing fibers, and aerosol hair sprays/foams based on these agents.

Keratin-containing fibers include all animal hair (e.g., wool, horsehair, angora hair, furs, feathers and products or fabrics produced from them). However, keratinic fibers preferably concern human hair.

Today, a suitably looking hairstyle is generally regarded as an essential part of a well groomed appearance. Based on actual fashion trends, time and again hairstyles are considered chic, which, for many types of hair, can only be formed or sustained over a longer period of up to several days by the use of certain consolidating materials. Thus, hair treatments, which provide a permanent or temporary hairstyling, play an important role. Temporary styling intended to provide a good hold, without compromising the healthy appearance of the hair, such as, for example the gloss, can be obtained for example by the use of hairsprays, hair waxes, hair gels, hair foams, setting lotions, etc.

Suitable compositions for temporary hairstyling usually contain synthetic polymers as the styling component. Preparations containing a dissolved or dispersed polymer can be applied on hair by propellants or by a pumping mechanism. Hair gels and hair waxes, however, are not generally applied directly on the hair, but rather dispersed with a comb or by hand.

An important property of an agent for temporary styling of keratin fibers, also referred to as styling agents, consists in giving the treated fibers the strongest possible hold for the shape created. If the keratinic fibers are human hair, then one also speaks of a strong hairstyle hold or high degree of hold of the styling agent. Styling hold can be determined by the type and quantity of synthetic polymer used, but other components of the styling agent may also influence hold.

In addition to a high degree of hold, styling agents must fulfill a whole series of additional requirements. These requirements can be broadly divided into hair properties, formulation properties (e.g., properties of the foam, gel or aerosol spray), and properties concerning the handling of the styling agent, with particular importance attached to the hair properties. These include moisture resistance, low stickiness and a balanced conditioning effect. Furthermore, a styling agent should be applicable for as many types of hair as possible.

In an attempt to meet the various requirements, various synthetic polymers have already been developed and are being used in styling agents. These polymers can be divided into cationic, anionic, non-ionic and amphoteric film-forming and/or setting polymers. Ideally these polymers form a polymer film when applied to hair, imparting a strong hold to the hairstyle while also being sufficiently flexible so as to not break under stress. If the polymer film is too brittle, film plaques develop (i.e., residues that are shed with movement of the hair and give the impression that the user of the respective styling agent has dandruff).

The development of styling agents that have all the desired properties still presents problems. This is particularly true for the combination of strong hold and simple, uniform application onto the keratin-containing fibers.

Accordingly, the present invention provides an agent for temporary shaping and/or care of keratinic fibers that has a high degree of hold or high care action, and in particular has excellent handleability during its application onto the keratin-containing fibers.

It has now been surprisingly found that this can be achieved by a combination of specific polymers. Furthermore, in the context of a specific embodiment of the invention, it was possible, in addition to these excellent properties, to provide compositions exempt from turbidity. Freedom from turbidity is of particular interest with respect to aerosol compositions, as solid suspended particles can block the discharge nozzle of the aerosol pack. Generally, for turbid and low viscosity compositions there is the additional danger of sedimentation that has a deleterious effect on storage stability of the composition.

Accordingly, a first subject matter of the present invention is an agent for treating keratin-containing fibers, especially human hair, comprising in a cosmetically acceptable carrier (a) at least one amphiphilic, cationic polymer having at least one structural unit according to Formula (I), at least one structural unit according to Formula (II), at least one structural unit according to Formula (III), and at least one structural unit according to Formula (IV),

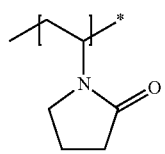

(I)

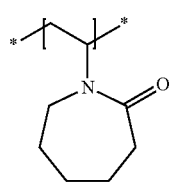

(II)

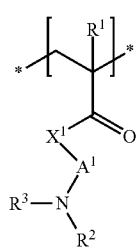

(III)

-continued

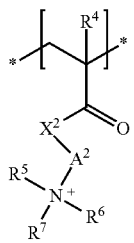
(IV)

wherein
R¹ and R⁴ are, independently of one another, a hydrogen atom or a methyl group,
X¹ and X² are, independently of one another, an oxygen atom or an NH group,
A¹ and A² are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group, and
$R^7$ is a ($C_8$ to $C_{30}$) alkyl group and
(b) at least one additional film-forming cationic and/or setting cationic polymer.

Film-forming polymers refer to those polymers that, on drying, leave a continuous film on the skin, hair or nails. These types of film-formers can be used in a wide variety of cosmetic products such as make up masks, make up, hair sets, hair sprays, hair gels, hair waxes, hair conditioners, shampoos or nail varnishes. Those polymers are particularly preferred which are sufficiently soluble in alcohol or water/alcohol mixtures, so that they are present in completely dissolved form in the agents. Film-forming polymers can be of synthetic or of natural origin.

According to the invention, film-forming polymers further refer to those polymers that, when used in concentrations of 0.1 to 20 wt. % in aqueous, alcoholic or aqueous alcoholic solution, are able to separate out a transparent polymer film on the hair.

Setting polymers contribute to hold and/or to the creation of hair volume and hair body of the whole hairstyle. These polymers are also film-forming polymers and therefore are generally typical substances for styling hair treatment compositions such as hair sets, hair foams, hair waxes, hair sprays. Film formation can be in completely selected areas and bond only some fibers together.

The curl-retention test or the three point bending tests are frequently used as a test method for the setting action of a polymer.

In the above Formulae and all Formulae below, the symbol * signifies a chemical bond that is a free valence of the corresponding structural fragment.

To compensate for the positive charge on the polymer in the agent, all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Exemplary ($C_1$ to $C_4$) alkyl groups are methyl, ethyl, propyl, isopropyl, butyl, sec-butyl, isobutyl, and tert-butyl.

Exemplary ($C_8$ to $C_{30}$) alkyl groups are octyl (capryl), decyl (caprinyl), dodecyl (lauryl), tetradecyl (myristyl), hexadecyl (cetyl), octadecyl (stearyl), eicosyl (arachyl), docosyl (behenyl).

Molecular weights of amphiphilic, cationic polymers according to the invention are preferably from 10,000 g/mol to 50,000,000 g/mol, especially from 50,000 g/mol to 5,000,000 g/mol, particularly preferably from 75,000 g/mol to 1,000,000 g/mol.

According to the invention, preferred agents contain amphiphilic, cationic polymers (a) in an amount of 0.1 wt. % to 20.0 wt. %, preferably 0.2 wt. % to 10.0 wt. %, more preferably 0.5 wt. % to 5.0 wt. %, based on total weight of the agent.

The properties of the agent have proven to be particularly advantageous when the agent is packaged as an aerosol spray, aerosol foam, pump spray or pump foam. This preferred packaging form is described later in detail.

The following amphiphilic, cationic polymers (a) are preferably used in agents according to the invention when the amphiphilic, cationic polymers (a) corresponding to the above Formulas (I) to (IV) fulfill one or more of the following criteria:
R¹ and R⁴ are each a methyl group,
X¹ is an NH group,
X² is an NH group,
A¹ and A² are, independently of one another, ethane-1,2-diyl or propane-1,3-diyl,
$R^2$, $R^3$, $R^5$ and $R^6$ are, independently of one another, methyl or ethyl (preferably methyl), and
$R^7$ is a ($C_{10}$ to $C_{24}$) alkyl group, especially decyl (caprinyl), dodecyl tetradecyl (myristyl), hexadecyl (cetyl), octadecyl (stearyl), eicosyl (arachyl) or docosyl (behenyl).

Preferably, the structural unit of Formula (III) is chosen from at least one of the structural units of Formulae (III-1) to (III-8)

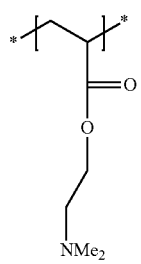
(III-1)

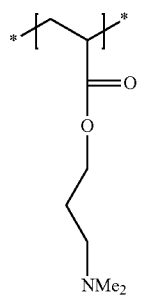
(III-2)

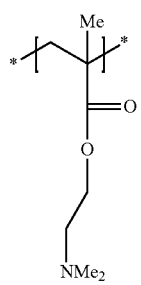
(III-3)

-continued (III-4)
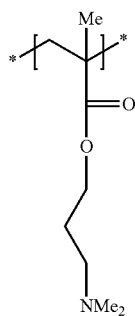

(III-5)
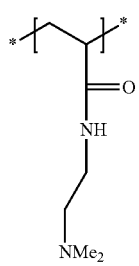

(III-6)
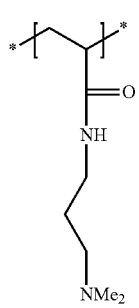

(III-7)
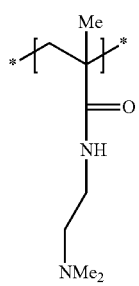

(III-8)
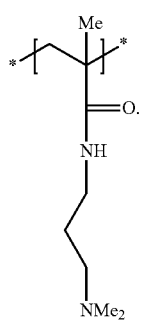

Moreover, it is particularly preferable to choose the structural unit according to Formula (III-7) and/or Formula (III-8) as the structural unit of Formula (III). According to the invention, the structural unit of Formula (III-8) is a quite particularly preferred structural unit.

Furthermore, the structural unit of Formula (IV) is preferably chosen from at least one structural unit of Formulae (IV-1) to (IV-8)

(IV-1)
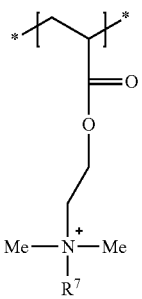

(IV-2)
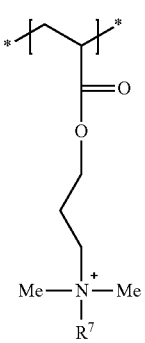

(IV-3)
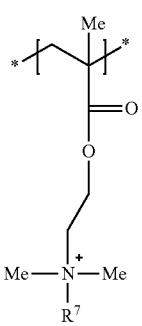

(VI-4)
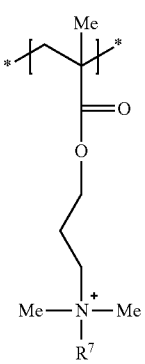

-continued

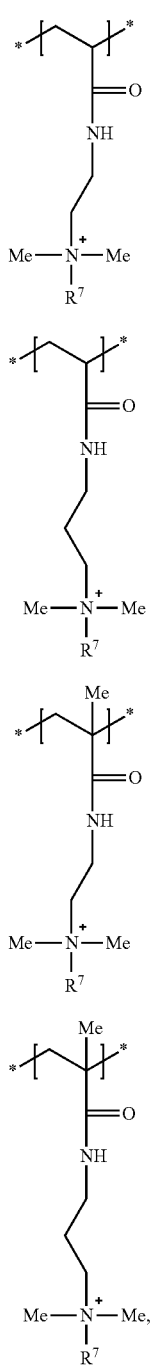

wherein each $R^7$ is a ($C_8$ to $C_{30}$) alkyl group.

Structural units of Formula (IV-7) and/or of Formula (IV-8) are again particularly preferred as the structural unit of Formula (IV), wherein each $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl). According to the invention, the structural unit of Formula (IV-8) represents a quite particularly preferred structural unit of Formula (IV).

An amphiphilic, cationic polymer having at least one structural unit of Formula (I), at least one structural unit of Formula (II), at least one structural unit of Formula (III-8), and at least one structural unit of Formula (IV-8) is quite particularly preferably present in the agent according to the invention.

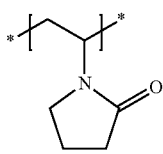

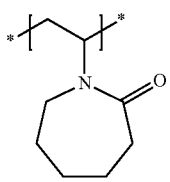

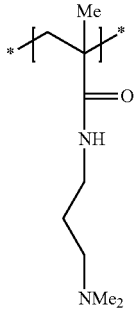

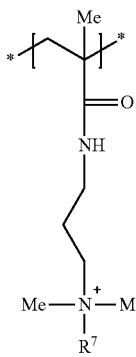

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl).

A quite particularly preferred amphiphilic, cationic polymer is the copolymer of N-vinyl pyrrolidone. N-vinyl caprolactam, N-(3-dimethylaminopropyl)methacrylamide and 3-(methacryloylamino)propy 1-lauryl-dimethylammonium chloride (INCI name: Polyquaternium-69), marketed, for example, under the trade name AquaStyle® 300 (28-32 wt. % active substance in an ethanol-water mixture, molecular weight 350 000) by the ISP company.

In addition, agents according to the invention further have at least one film-forming cationic and/or setting cationic polymer. These polymers differ from the amphiphilic, cationic polymers (a).

In this regard, it is again preferred that the agent have at least two additional film-forming cationic and/or setting cationic polymers as component (b). These two additional film-forming cationic and/or setting cationic polymers differ from each another as well as from the amphiphilic, cationic polymers (a).

The additional film-forming cationic and/or setting cationic polymers preferably has at least one structural unit having at least one permanently cationized nitrogen atom.

"Permanently canonized nitrogen atoms" refers to those nitrogen atoms that carry a positive charge and thereby form a quaternary ammonium compound. Quaternary ammonium compounds are mostly produced by reacting tertiary amines with alkylating agents, such as methyl chloride, benzyl chloride, dimethyl sulfate, dodecyl bromide, and ethylene oxide. Depending on the tertiary amine, the following groups are particularly well known: alkylammonium compounds, alkenylammonium compounds, imidazolinium compounds and pyridinium compounds.

According to the invention, preferred agents contain film-forming, cationic anchor setting cationic polymers (b) in an amount of 0.1 wt. % to 20.0 wt. %, preferably 0.2 wt. % to 10.0 wt. %, and more preferably 0.5 wt. % to 5.0 wt. %, based on total weight of the agent.

According to the invention, cationic film-forming and/or cationic setting polymers can be chosen from cationic, quaternized cellulose derivatives.

Agents corresponding to this embodiment form turbid compositions. Turbidity can be seen with the naked eye. Moreover, agents of this embodiment additionally have advantageous parameters with respect to the strong degree of hold for the hairstyle or volume or for haircare.

In the context of this embodiment, those agents are suitable that have, in a cosmetically acceptable carrier (a) at least one amphiphilic, cationic polymer having at least one structural unit of Formula (I), at least one structural unit of Formula (II), at least one structural unit of Formula (III), and at least one structural unit of Formula (IV),

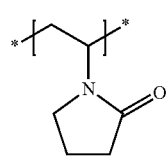
(I)

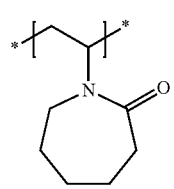
(II)

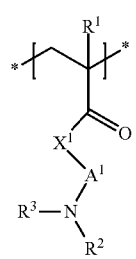
(III)

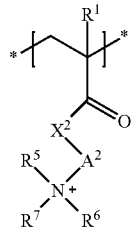
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional film-forming cationic and/or setting cationic polymer chosen from cationic, quaternized cellulose derivatives.

Accordingly, in the context of this embodiment, those particular agents are suitable that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8)

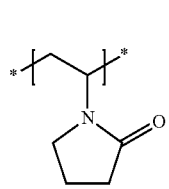
(I)

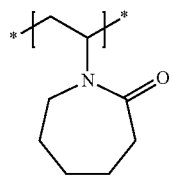
(II)

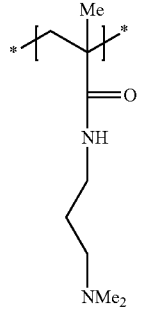
(III-8)

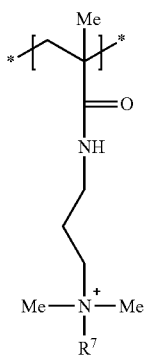

(IV-8)

wherein R⁷ is cetyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives.

In general, those cationic, quaternized celluloses having more than one permanent cationic charge in a side chain have proven to be advantageous.

Among the cationic cellulose derivatives to be highlighted are those produced from the reaction of hydroxyethyl cellulose with a dimethyldiallylammonium reactant (especially dimethyldiallylammonium chloride), optionally in the presence of further reactants. Among these cationic celluloses, once again those cationic celluloses with the INCI name Polyquaternium-4 are particularly suitable, which, for example, are marketed by the National Starch Company under the trade names Celquat® H 100, Celquat® L 200.

Consequently, in the context of this embodiment, agents according to the invention are suitable that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8)

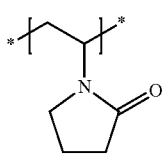

(I)

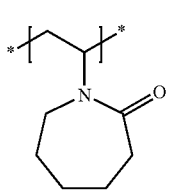

(II)

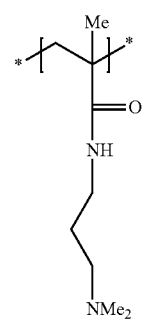

(III-8)

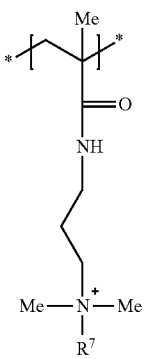

(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives produced from the reaction of hydroxyethyl cellulose with a dimethyldiallylammonium reactant (especially dimethyldiallylammonium chloride), optionally in the presence of further reactants.

It is again particularly preferred for the abovementioned preferred embodiments when agents according to the invention have at least one additional film-forming cationic and/or setting cationic polymer different from the polymers defined under (a) and (b).

In the context of these abovementioned embodiments, the previously cited preferred embodiments of amphiphilic, cationic polymer (a) are suitable (see above). Similarly, all previously mentioned preferred quantitative data with respect to polymer components (a) and (b) of the agent are also well suited mutatis mutandis for these embodiments.

In addition, such cationic film-forming and/or cationic setting polymers having at least one structural unit of Formula (I), at least one structural unit of Formula (V), and at least one structural unit of Formula (VI) are suitable

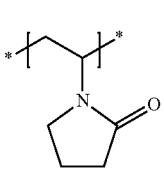

(I)

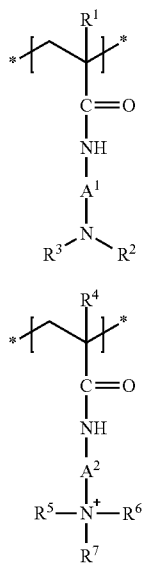

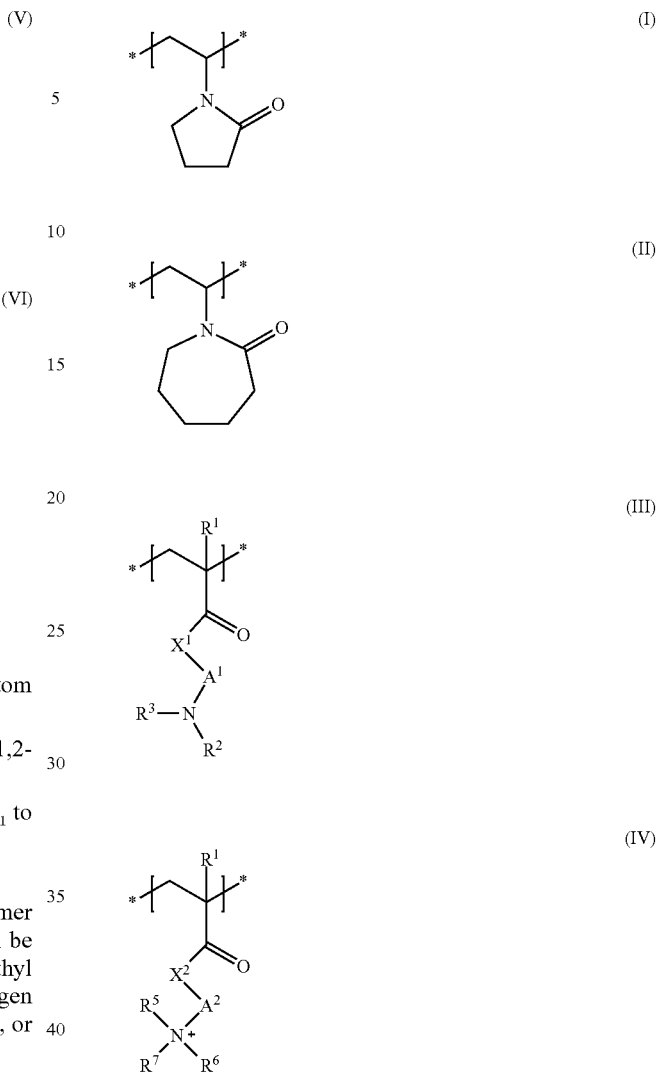

wherein

R¹ and R⁴ are, independently of one another, a hydrogen atom or a methyl group,

A¹ and A² are, independently of one another, an ethane-1,2-diyl, propane-1,3-diyl or butane-1,4-diyl group, R², R³, R⁵ and R⁶ are, independently of one another, a ($C_1$ to $C_4$) alkyl group, R⁷ is a ($C_8$ to $C_{30}$) alkyl group.

To compensate for the positive charge of the monomer (VI), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Exemplary suitable compounds are copolymers of dimethylaminoethyl methacrylate quaternized with diethyl sulfate, with vinyl pyrrolidone having the INCI name Polyquaternium-11, available under the trade names Gafquat® 440, Gafquat® 734, Gafquat® 755 (each from ISP) and Luviquat PQ 11 PN (BASF SE), copolymers of methacryloylaminopropyllauryldimethylammonium chloride with vinyl pyrrolidone and dimethylaminopropylmethacrylamide with the INCI name Polyquaterniumn-55, commercially available under the trade names, Styleze® W-10, Styleze® W-20 (ISP).

Agents corresponding to this embodiment form turbid compositions. Turbidity can be seen with the naked eye. Moreover, agents of this embodiment additionally have acceptable parameters regarding the strong degree of hold for the hairstyle or the volume or for haircare.

Accordingly, those agents are suitable that have, in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV), wherein R¹ and R⁴ are, independently of one another, a hydrogen atom or a methyl group, X¹ and X² are, independently of one another, an oxygen atom or an NH group, A¹ and A² are, independently of one another, an ethane-1, 2-diyl, propane-1,3-diyl or butane-1,4-diyl group, R², R³, R⁵ and R⁶ are, independently of one another, a ($C_1$ to $C_4$) alkyl group, and R⁷ is a ($C_8$ to $C_{30}$) alkyl group, and (b) at least one additional cationic film-forming and/or cationic setting polymer having at least one structural unit of Formula (I), at least one structural unit of Formula (V), and at least one structural unit of Formula (VI)

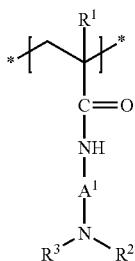 (V)

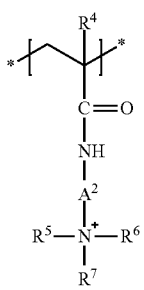 (VI)

wherein
$R^1$ and $R^4$ are, independently of one another, a hydrogen atom or a methyl group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group,
$R^7$ is a ($C_8$ to $C_{30}$) alkyl group.

In addition, those agents are suitable that have, in a cosmetically acceptable carrier
(a) at least one amphiphilic, cationic polymer having at least one structural unit of Formula (I), at least one structural unit of Formula (II), at least one structural unit of Formula (III-8), and at least one structural unit of Formula (IV-8)

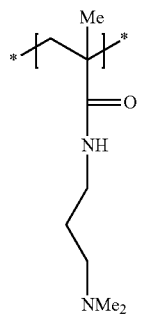 (III-8)

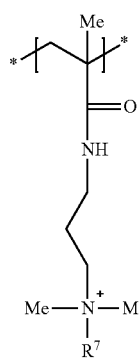 (IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and
(b) at least one additional cationic film-forming and/or cationic setting polymer having at least one structural unit of Formula (I), at least one structural unit of Formula (V), and at least one structural unit of Formula (VI)

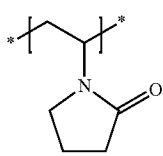 (I)

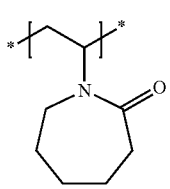 (II)

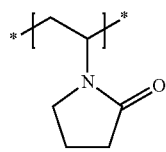 (I)

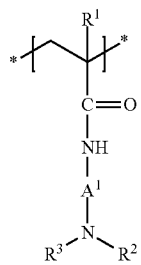 (V)

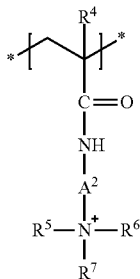

(VI)

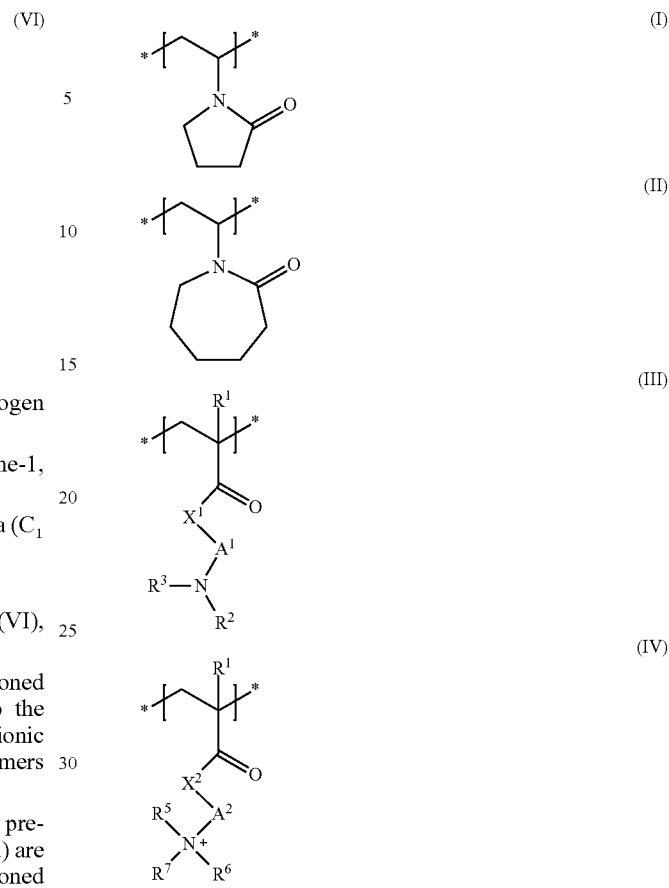

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, and $R^7$ is a ($C_8$ to $C_{30}$) alkyl group.

To compensate for the positive charge of monomer (VI), the above relevant statement applies.

It is again particularly preferred for the abovementioned preferred embodiments when the agent according to the invention has at least one additional film-forming cationic and/or setting cationic polymer different from the polymers defined under (a) and (b).

According to this embodiment, the previously cited preferred embodiments of amphiphilic, cationic polymer (a) are preferred (see above). Similarly, all previously mentioned quantitative data regarding polymer components (a) and (b) of the agent are also preferred mutatis mutandis for these embodiments.

In the context of the invention, additionally, those cationic film-forming and/or cationic setting copolymers (b) having at least one structural element of Formula (M1) serve as a particularly preferred usable film-forming and/or setting polymers chosen from cationic polymers having at least one structural unit possessing a permanently cationized nitrogen atom (M1)

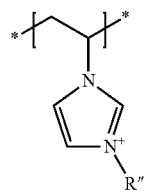

wherein R" is a ($C_1$ to $C_4$) alkyl group, especially a methyl group, and additionally having another cationic and/or non-ionic structural element.

Accordingly, in the context of the present invention, those agents are particularly preferred that have, in a cosmetically acceptable carrier (a) at least one amphiphilic, cationic polymer having at least one structural unit of Formula (I), at least one structural unit of Formula (II), at least one structural unit of Formula (III), and at least one structural unit of Formula (IV), wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional cationic film-forming and/or cationic setting polymer having at least one structural element of Formula (M1) as the at least one structural unit having a permanently cationized nitrogen atom (M1)

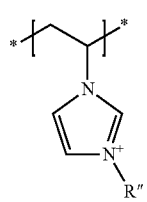

wherein

R" is a ($C_1$ to $C_4$) alkyl group, especially a methyl group, and additionally has another cationic and/or non-ionic structural element.

It is again particularly preferred for the abovementioned preferred embodiments when the agent has at least one additional film-forming cationic and/or setting cationic polymer different from polymers (a) and (b).

Agents according to this embodiment form transparent (i.e., non-turbid) compositions. Any turbidity cannot be seen with the naked eye. Moreover, the agents also have to an excellent degree the advantageous parameters regarding the strong degree of hold for the hairstyle or volume or for haircare.

To compensate for the positive polymer charge of component (b), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

According to this embodiment, those agents are particularly preferred that have, in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8)

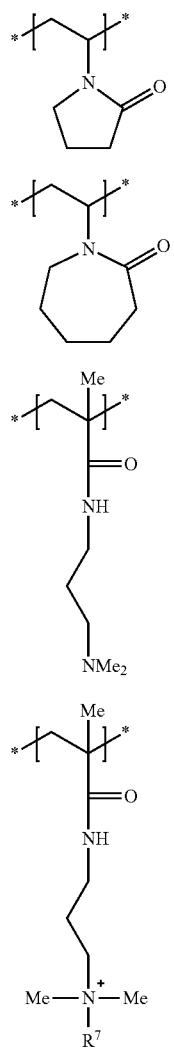

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one cationic film-forming and/or cationic setting polymer having at least one structural element of Formula (M1)

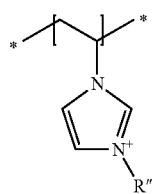

wherein R" is a ($C_1$ to $C_4$) alkyl group, especially a methyl group, and additionally has another cationic and/or non-ionic structural element.

It is again particularly preferred for the abovementioned preferred embodiments when the agent has at least one additional film-forming cationic and/or setting cationic polymer different from polymers defined under (a) and (b).

In particular, the previously mentioned polymer with the INCI name Polyquaternium 69 is particularly preferred as the amphiphilic cationic polymer (a) (see above).

To compensate for the positive polymer charge of component (b), the above relevant statement applies.

It is again inventively preferred when, in addition to amphiphilic cationic polymer (a), the agent contains at least one copolymer (b1) containing, in addition to a structural element of Formula (M1), a structural element of Formula (I) as the cationic film-forming and/or cationic setting polymer (b)

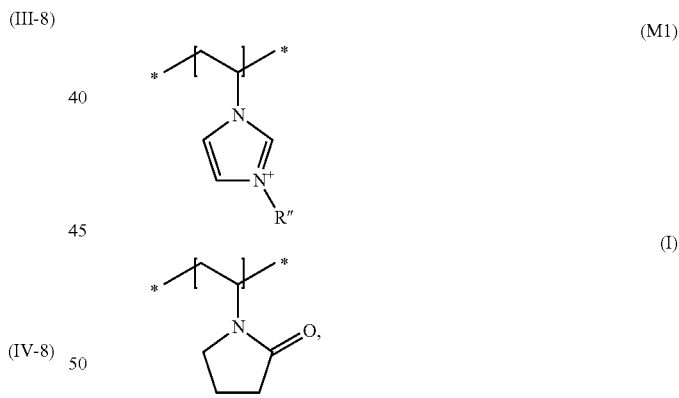

wherein R" is a ($C_1$ to $C_4$) alkyl group, particularly a methyl group.

To compensate for the positive polymer charge of copolymer (b1), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Quite particularly preferred cationic film-forming and/or cationic setting polymers as copolymers (b1) have 1 to 30 mol %, preferably 15 to 25 mol % and particularly 20 mol % of structural units according to Formula (M1), and 70 to 90 mol %, preferably 75 to 85 mol % and particularly 80 mol % of structural units according to Formula (I).

Accordingly, it is particularly preferred when copolymers (b1) have, in addition to polymer units resulting from the incorporation of the cited structural units according to Formula (M1) and (I) into the copolymer, a maximum of 5 wt. %, preferably a maximum of 1 wt. % of polymer units that trace back to the incorporation of other monomers. Copolymers (b1) are preferably exclusively formed from structural units of Formula (M1) wherein R″=methyl and (I), and can be described by the general Formula (Poly1)

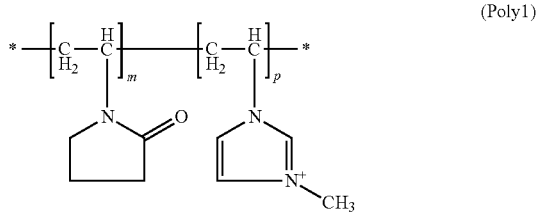

(Poly1)

wherein indices m and p vary according to the molecular mass of the polymer and are not intended to mean to portray block copolymers. In fact, structural units of Formula (M1) and Formula (I) can be statistically distributed in the molecule.

If a chloride ion is used to compensate for the positive charge of the polymer of Formula (Poly1), then these N-methyl vinylimidazole/vinyl pyrrolidone copolymers are named according to INCI nomenclature as Polyquaternium-16 and are available from, for example, BASF under the trade names Luviquat® Style, Luviquat® FC 370, Luviquat® FC 550, Luviquat® FC 905 and Luviquat® HM 552. If a methosulfate ion is used to compensate for the positive charge of the polymer of Formula (Poly1), then these N-methyl vinylimidazole/vinyl pyrrolidone copolymers are named according to INCI nomenclature as Polyquaternium-44 and are available from for example BASF under the trade name Luviquat® UltraCare.

Particularly preferred inventive agents contain a copolymer (b1), especially of Formula (Poly1), having molecular masses within a defined range. Here, preferred agents have a molecular mass of copolymer (b1) from 50 to 400 kDa, preferably from 100 to 300 kDa, more preferably from 150 to 250 kDa, and particularly from 190 to 210 kDa.

In addition to copolymer(s) b1 or instead of it or them, the agents can also contain copolymers (b2) having as additional structural units structural units of Formula (II)

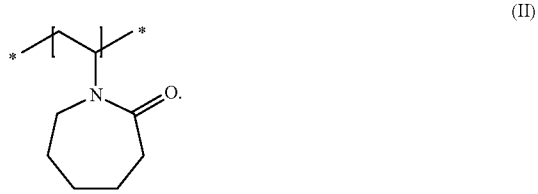

(II)

Further particularly preferred agents according to the invention are those that have as the cationic film-forming and/or cationic setting polymer (b) at least one copolymer (b2) that has at least one structural unit according to Formula (M1-a), at least one structural unit according to Formula (I), and at least one structural unit according to Formula (II)

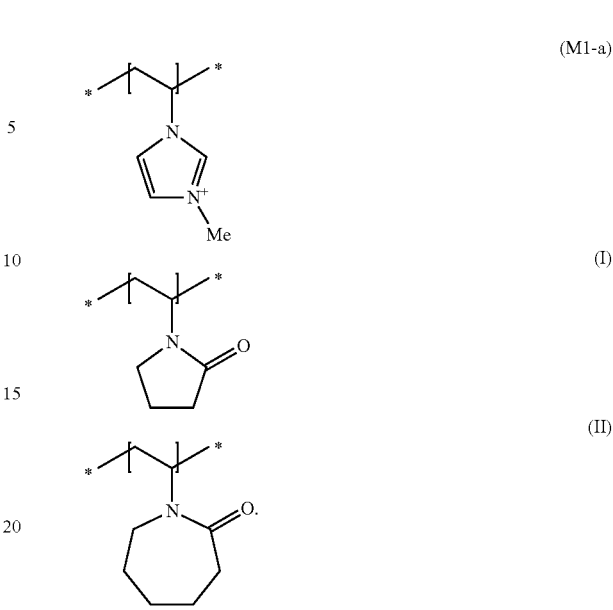

(M1-a)

(I)

(II)

Also, it is particularly preferred when copolymers (b2) have, in addition to polymer units resulting from the incorporation of the cited structural units according to Formula (M1-a), (I) and (II) into the copolymer, a maximum of 5 wt. %, preferably a maximum of 1 wt. % of polymer units that trace back to the incorporation of other monomers. Copolymers (b2) are preferably exclusively formed from structural units of Formula (M1-a), (I) and (II) can be described by the general Formula (Poly2)

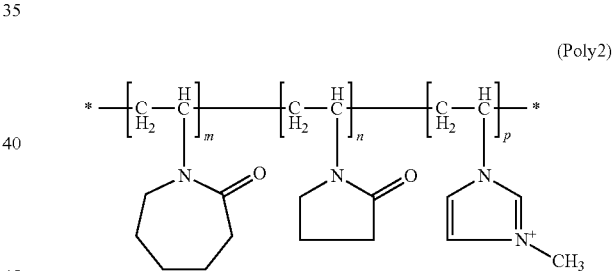

(Poly2)

wherein indices m, n and p vary according to the molecular mass of the polymer and are not intended to mean to portray block copolymers. In fact, structural units of the cited Formulas can be statistically distributed in the molecule.

To compensate for the positive polymer charge of component (b2), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

If a methosulfate ion is used to compensate the positive charge of the polymer of Formula (Poly2), then these N-methyl vinylimidazole/vinyl pyrrolidone/vinyl caprolactam copolymers are named according to INCI nomenclature as Polyquaternium-46 and are available from, for example, BASF under the trade name Luviquat® Hold.

Quite particularly preferred copolymers (b2) contain 1 to 20 mol %, preferably 5 to 15 mol % and particularly 10 mol % of structural units according to Formula (M1-a), 30 to 50 mol %, preferably 35 to 45 mol % and particularly 40 mol % of structural units according to Formula (I), and 40 to 60 mol %, preferably 45 to 55 mol % and particularly 60 mol % of structural units according to Formula (II).

Particularly preferred inventive agents contain a copolymer (b2) having molecular masses within a defined range. Here, agents wherein the molecular mass of copolymer (b2) is from 100 to 1000 kDa, preferably from 250 to 900 kDa, more preferably from 500 to 850 kDa and particularly from 650 to 710 kDa are preferred.

In addition to copolymer(s) (b1) and/or (b2) or in its or their place, agents according to the invention can also include copolymers (b3) as the film-forming cationic and/or setting cationic polymer (b) having as structural units structural units of Formulas (M1-a) and (I), as well as structural units from the group of vinyl imidazole units and further structural units from the group of acrylamide and/or methacrylamide units.

Further particularly preferred agents contain as the cationic film-forming and/or cationic setting polymer (b) at least one copolymer (b3) having at least one structural unit according to Formula (M1-a), at least one structural unit according to Formula (I), at least one structural unit according to Formula (VI), and at least one structural unit according to Formula (VII)

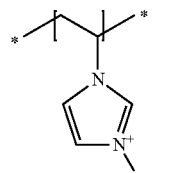

(M1-a)

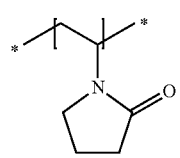

(I)

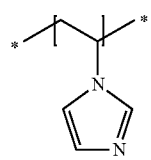

(VI)

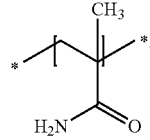

(VII)

Also, it is particularly preferred when copolymers (b3) contain, in addition to polymer units resulting from the incorporation of the cited structural units according to Formula (M1-a), (I), (VI) and (VII) into the copolymer, a maximum of 5 wt. %, preferably a maximum of 1 wt. % of polymer units that trace back to the incorporation of other monomers. Copolymers (b3) are preferably exclusively formed from structural units of Formula (M1-a), (I), (VI) and (VII) and can be described by the general Formula (Poly3)

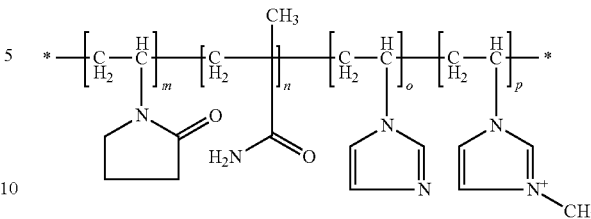

(Poly3)

wherein indices m, n, o and p vary according to the molecular mass of the polymer and are not intended to mean to portray block copolymers. In fact, structural units of Formula (M1-a), (I), (VI) and (VII) can be statistically distributed in the molecule.

To compensate for the positive polymer charge of component (b2), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

If a methosulfate ion is used to compensate the positive charge of the polymer of Formula (Poly3), then these N-methyl vinylimidazole/vinyl pyrrolidone/vinyl imidazole/methacrylamide copolymers are named according to INCI nomenclature as Polyquaternium-68 and are available from, for example, BASF under the trade name Luviquat® Supreme.

Quite particularly preferred copolymers (b3) contain 1 to 12 mol %, preferably 3 to 9 mol %, and particularly 6 mol % of structural units according to Formula (M1-a), 45 to 65 mmol %, preferably 50 to 60 mol %, and particularly 55 mol % of structural units according to Formula (I), 1 to 20 mol %, preferably 5 to 15 mol %, and particularly 10 mol % of structural units according to Formula (VI), and 20 to 40 mol %, preferably 25 to 35 mol %, and particularly 29 mol % of structural units according to Formula (VII).

Particularly preferred inventive agents contain a copolymer (b3) having molecular masses within a defined range. Here, inventive agents are preferred wherein the molecular mass of copolymer (b3) is from 100 to 500 kDa, preferably from 150 to 400 kDa, more preferably from 250 to 350 kDa, and particularly from 290 to 310 kDa.

Preferred additional film-forming cationic and/or setting polymers chosen from cationic polymers (b) having at least one structural element of the above Formula (M1) are: vinyl pyrrolidone/1-vinyl-3-methyl-1H-imidazolium chloride copolymers (such as that with the INCI name Polyquaternium-16 sold under the trade names Luviquat® Style, Luviquat® FC 370, Luviquat® FC 550, Luviquat® FC 905 and Luviquat® HM 552 (BASF SE)), vinyl pyrrolidone/1-vinyl-3-methyl-1H-imidazolium methylsulfate copolymers (such as for example that with the INCI name Polyquaternium-44 sold under the trade name Luviquat® Care (BASF SE)), vinyl pyrrolidone/vinyl caprolactam 1-vinyl-3-methyl-1H-imidazolium terpolymer (such as for example that with the INCI name Polyquaternium-46 sold under the trade names Luviquat® Care or Luviquat® Hold (BASF SE)), vinyl pyrrolidone/methacrylamide/vinyl imidazole/1-vinyl-3-methyl-1H-imidazolium methyl sulfate copolymer (such as for example that with the INCI name Polyquaternium-68 sold under the trade name Luviquat® Supreme (BASF SE)), as well as mixtures of these polymers.

In the case where the agent has, in addition to amphiphilic, cationic polymer (a), two different cationic film-forming and/ or cationic setting polymers (b), then the following embodiments have proven particularly suitable.

In a preferred embodiment, agents contain, in a cosmetically acceptable carrier
(a) at least one amphiphilic, cationic polymer having at least one structural unit of Formula (I), at least one structural unit of Formula (II), at least one structural unit of Formula (III), and at least one structural unit of Formula (IV),

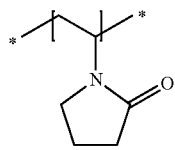
(I)

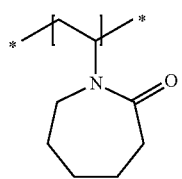
(II)

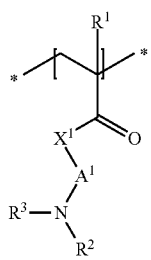
(III)

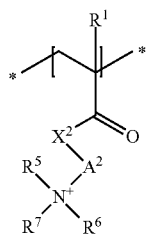
(IV)

wherein
R$^1$ and R$^4$ are, independently of one another, a hydrogen atom or a methyl group,
X$^1$ and X$^2$ are, independently of one another, an oxygen atom or an NH group,
A$^1$ and A$^2$ are, independently of one another, an ethane-1, 2-diyl, propane-1,3-diyl or butane-1,4-diyl group,
R$^2$, R$^3$, R$^5$ and R$^6$ are, independently of one another, a (C$_1$ to C$_4$) alkyl group, and
R$^7$ is a (C$_8$ to C$_{30}$) alkyl group, and
(bI) at least one cationic film-forming and/or cationic setting polymer having at least one structural element of Formula (M1)

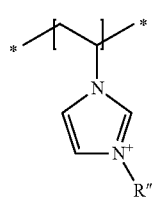
(M1)

wherein R" is a (C$_1$ to C$_4$) alkyl group, especially methyl, and
additionally has another cationic and/or non-ionic structural element, and
(bII) at least one cationic film-forming and/or cationic setting polymer having at least one structural unit of Formula (I), at least one structural unit of Formula (V), and at least one structural unit of Formula (VI)

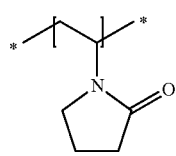
(I)

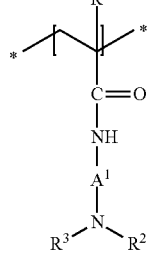
(V)

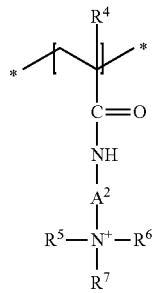
(VI)

wherein
R$^1$ and R$^4$ are, independently of one another, a hydrogen atom or a methyl group,
A$^1$ and A$^2$ are, independently of one another, an ethane-1, 2-diyl, propane-1,3-diyl or butane-1,4-diyl group,
R$^2$, R$^3$, R$^5$ and R$^6$ are, independently of one another, a (C$_1$ to C$_4$) alkyl group, and
R$^7$ is a (C$_8$ to C$_{30}$) alkyl group.

In a preferred embodiment, agents contain, in a cosmetically acceptable carrier
(a) at least one amphiphilic, cationic polymer having at least one structural unit of Formula (I), at least one structural unit of Formula (II), at least one structural unit of Formula (III-8), and at least one structural unit of Formula (IV-8)

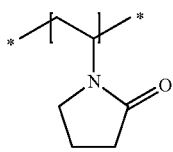
(I)

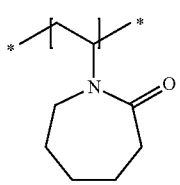
(II)

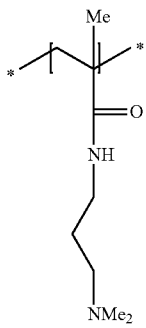
(III-8)

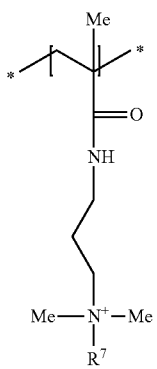
(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (bI) at least one cationic film-forming and/or cationic setting polymer having at least one structural element of Formula (M1) and at least one structural element of Formula (I)

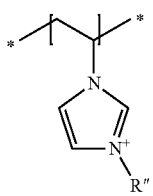
(M1)

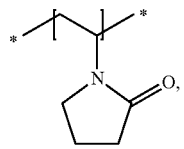
(I)

wherein R″ is a ($C_1$ to $C_4$) alkyl group, particularly methyl, and (bII) at least one cationic film-forming and/or cationic setting polymer having at least one structural unit of Formula (I), at least one structural unit of Formula (V), and at least one structural unit of Formula (VI)

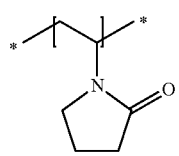
(I)

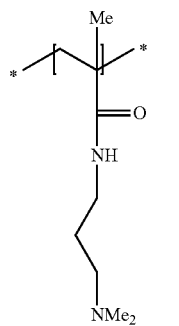
(III-8)

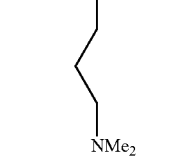

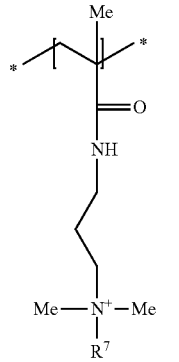
(IV-8)

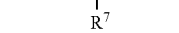

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl).

In this regard, quite particularly preferred agents include (polymers defined by the relevant INCI name) Polyquaternium-69, (bI) Polyquaternium-16, (b-II) Polyquaternium-55.

In the context of this embodiment, the previously cited preferred embodiments of the amphiphilic, cationic polymer (a) are preferred (see above). Similarly, all the previously mentioned quantitative data regarding polymer components (a) and (bI) of the agent are also preferred mutatis mutandis for these embodiments.

The preferred embodiments described above again allow the following particularly preferred embodiment to be made which provides particularly preferred technical effects for achieving the technical object of the invention.

Accordingly, in the context of the present invention, those agents are particularly preferred that have in a cosmetically acceptable carrier (a) at least one amphiphilic, cationic polymer having at least one structural unit of Formula (I), at least one structural unit of Formula (II), at least one structural unit of Formula (III), and at least one structural unit of Formula (IV),

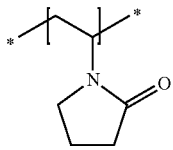
(I)

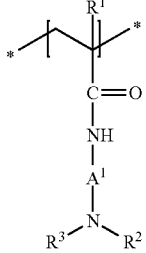
(II)

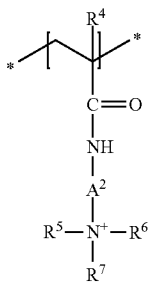
(III)

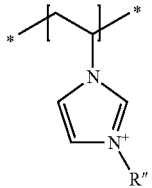
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, and $R^7$ is a ($C_8$ to $C_{30}$) alkyl group, and (bI) at least one cationic film-forming and/or cationic setting polymer chosen from a polymer (b1) or (b2) or (b3)—

(b1) cationic, quaternized cellulose derivatives, (b2) polymers having at least one structural unit of Formula (I), at least one structural unit of Formula (V), and at least one structural unit of Formula (VI)

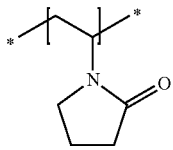
(I)

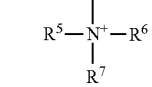
(V)

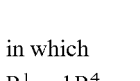
(VI)

in which $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, and $R^7$ is a ($C_8$ to $C_{30}$) alkyl group, or (b3) polymers having at least one structural element of Formula (M1)

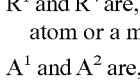
(M1)

wherein R″ is a ($C_1$ to $C_4$) alkyl group, especially a methyl group, and additionally at least a further cationic and/or non-ionic structural element, (bII) at least one cationic film-forming and/or cationic setting polymer that is different from (a) and (bI) and is chosen from at least one polymer of cationic, quaternized cellulose derivatives polymers having at least one structural unit of Formula (I), at least one structural unit of Formula (V), and at least one structural unit of Formula (VI)

(a) at least one amphiphilic, cationic polymer having at least one structural unit of Formula (I), at least one structural unit of Formula (II), at least one structural unit of Formula (III), and at least one structural unit of Formula (IV),

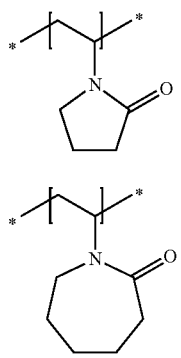
(I)

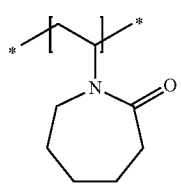
(II)

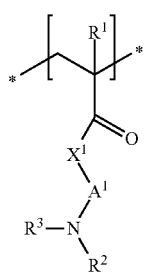
(III)

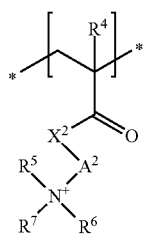
(IV)

wherein
$R^1$ and $R^4$ are, independently of one another, a hydrogen atom or a methyl group,
$X^1$ and $X^2$ are, independently of one another, an oxygen atom or an NH group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group,
$R^7$ is a ($C_8$ to $C_{30}$) alkyl group, and (bI) at least one cationic film-forming and/or cationic setting polymer chosen from at least one cationic, quaternized cellulose derivative, and (bII) at least one cationic film-forming and/or cationic setting polymer different from (a) and (b) and is chosen from at least one polymer of the group of polymers having at least one structural unit of Formula (I), at least one structural unit of Formula (V), and at least one structural unit of Formula (VI)

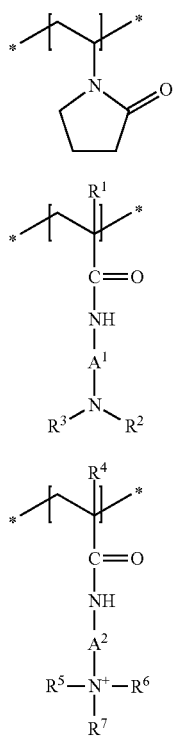

(I)

(V)

(VI)

wherein
$R^1$ and $R^4$ are, independently of one another, a hydrogen atom or a methyl group,
A1 and A2 are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group, and
$R^7$ is a ($C_8$ to $C_{30}$) alkyl group,
polymers having at least one structural element of Formula (M1)

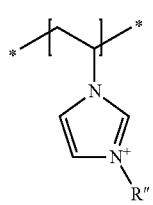
(M1)

in which R" is a ($C_1$ to $C_4$) alkyl group, especially a methyl group, and
additionally having another cationic and/or non-ionic structural element.

Preferably, the polymers (bI) are incorporated in the agent in an amount of 0.1 wt. % to 15 wt. %, more preferably 0.25 wt. % to 5.0 wt. %, based on total weight of the agent.

Preferably, the polymers (bII) are incorporated in the agent according to the invention in an amount of 0.1 wt. % to 15 wt. %, more preferably 0.1 wt. % to 10.0 wt. %, quite particularly preferably 0.25 wt. % to 5.0 wt. %, based on total weight of the agent.

The following agents are suitable for achieving the technical object having, in a cosmetically acceptable carrier

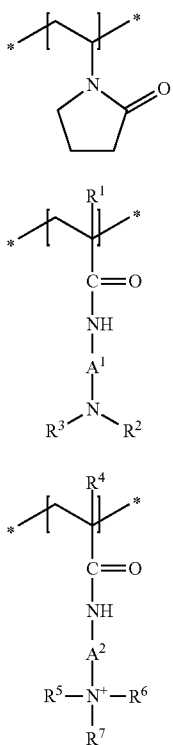

(I)

(V)

(VI)

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, polymers having at least one structural element of Formula (M1)

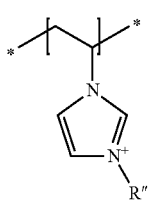

(M1)

wherein R" is a ($C_1$ to $C_4$) alkyl group, especially a methyl group, and additionally having another cationic and/or non-ionic structural element.

In this regard, those agents are preferably suitable that have, in an a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

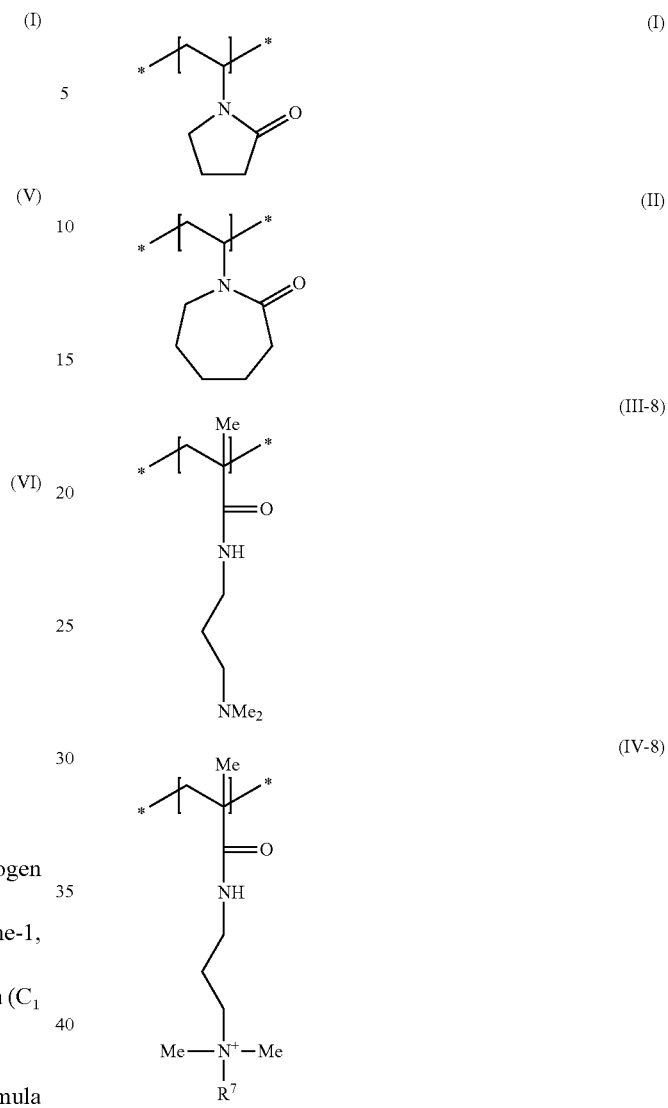

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (bI) at least one cationic film-forming and/or cationic setting polymer chosen from at least one cationic, quaternized cellulose derivative (especially Polyquaternium-4), and (bII) at least one cationic film-forming and/or cationic setting polymer different from (a) and (b) and is chosen from at least one polymer of the group of polymers having at least one structural unit of Formula (I), at least one structural unit of Formula (V), and at least one structural unit of Formula (VI)

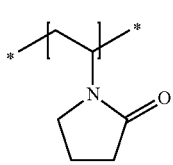

(I)

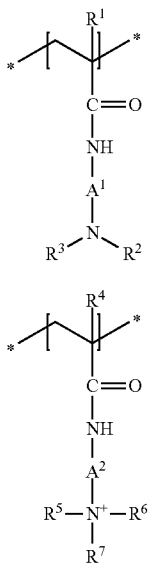

(V)

(VI)

wherein
R¹ and R⁴ are, independently of one another, a hydrogen atom or a methyl group,
A¹ and A² are, independently of one another, an ethane-1,2-diyl, propane-1,3-diyl or butane-1,4-diyl group,
R², R³, R⁵ and R⁶ are, independently of one another, a ($C_1$ to $C_4$) alkyl group,
R⁷ is a ($C_8$ to $C_{30}$) alkyl group.

In the context of this embodiment, the previously cited preferred embodiments of the amphiphilic, cationic polymer (a) are preferred (see above).

The following preferred agents are quite particularly preferably suitable which have in a cosmetic carrier at least one of the following polymer combinations (defined by the relevant INCI name):
(a) Polyquaternium-69 (bI) Polyquaternium-4 (bII) Polyquaternium-55,
(b) Polyquaternium-69 (bI) Polyquaternium-4 (bII) Polyquaternium-16

Similarly, all previously mentioned quantitative data regarding polymer components (a) and (bI) and (bII) of the agent are also preferred mutatis mutandis for these embodiments.

In addition to the added additional film-forming cationic and/or setting polymer chosen from cationic polymers having at least one structural unit possessing a permanently cationized nitrogen atom, the agents can have at least one further film-forming and/or setting polymer different from polymers (a) and (b).

In order to intensify the effect according to the invention, the agents preferably additionally have at least one surfactant, with non-ionic, anionic, cationic, and ampholytic surfactants being suitable. The group of ampholytic or amphoteric surfactants includes zwitterionic surfactants and ampholytes. According to the invention, the surfactants can already have an emulsifying action.

The agent preferably contains additional surfactants in an amount of 0.01 wt. % to 5 wt. %, more preferably 0.05 wt. % to 0.5 wt. %, based on total weight of the agent.

It has proved particularly preferable when agents according to the invention have at least one non-ionic surfactant.

Non-ionic surfactants contain, for example, a polyol group, a polyalkylene glycol ether group or a combination of polyol ether groups and polyglycol ether groups as the hydrophilic group.

Exemplary compounds of this type are
addition products of 2 to 100 moles ethylene oxide and/or 1 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group,
methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as, for example, the commercially available types Dehydrol® LS, Dehydrol® LT (Cognis),
$C_{12}$-$C_{30}$ fatty acid mono- and diesters of addition products of 1 to 30 moles ethylene oxide to glycerin,
addition products of 5 to 60 moles ethylene oxide on castor oil and hydrogenated castor oil,
polyol esters of fatty acids, such as, for example, the commercial product Hydagen® HSP (Cognis) or Sovermol types (Cognis),
alkoxylated triglycerides,
alkoxylated fatty acid alkyl esters of the formula (E4-I)

$$R^1CO-(OCH_2CHR^2)_wOR^3 \qquad (E4\text{-}I)$$

wherein $R^1CO$ is a linear or branched, saturated and/or unsaturated acyl group containing 6 to 22 carbon atoms, $R^2$ is hydrogen or methyl, $R^3$ is linear or branched alkyl groups containing 1 to 4 carbon atoms, and w is a number from 1 to 20,
amine oxides,
mixed hydroxy ethers such as are described in DE-OS 1 973 8866,
sorbitol esters of fatty acids and addition products of ethylene oxide to sorbitol esters of fatty acids such as e.g. the polysorbates,
sugar esters of fatty acids and addition products of ethylene oxide to sugar esters of fatty acids,
addition products of ethylene oxide to fatty acid alkanolamides and fatty amines,
sugar surfactants of the type alkyl and alkenyl oligoglycosides according to Formula (E4-II),

$$R^4O-[G]_p \qquad (E4\text{-}I)$$

wherein $R^4$ is an alkyl or alkenyl group containing 4 to 22 carbon atoms, G is a sugar group containing 5 or 6 carbon atoms, and p is a number from 1 to 10. They can be obtained according to the appropriate methods of preparative organic chemistry.

The alkyl and alkenyl oligoglycosides can derive from aldoses or ketoses containing 5 or 6 carbon atoms, preferably from glucose. Preferred alkyl and/or alkenyl oligoglycosides are accordingly alkyl and/or alkenyl oligoglucosides The index value p in the general Formula (E4-II) represents the degree of oligomerization (DP) (i.e., the distribution of mono and oligoglycosides), and is a number from 1 to 10. Whereas in a given compound p must always be a whole number, and here above all can assume the values p=1 to 6, the value p for a specific alkyl oligoglycoside is an analytically determined calculated quantity that mostly represents a fractional number. Preferably, alkyl and/or alkenyl oligoglycosides are employed with an average degree of oligomerization p of 1.1 to 3.0. From an industrial point of view, such alkyl and/or alkenyl oligoglycosides are preferred with degrees of oligomerization less than 1.7 and in particular between 1.2 and 1.4.

Alkylene oxide addition products to saturated, linear fatty alcohols and fatty acids, each with 2 to 100 moles ethylene oxide per mole fatty alcohol or fatty acid, are particularly preferred non-ionic surfactants. Similarly, preparations with excellent properties are obtained when they contain $C_{12}$-$C_{30}$ fatty acid mono- and diesters of addition products of 1 to 30 moles ethylene oxide to glycerin and/or addition products of 5 to 60 moles ethylene oxide to castor oil and hydrogenated castor oil as the non-ionic surfactants.

For surfactants represented by the addition products of ethylene oxide and/or propylene oxide to fatty alcohols or derivatives of these addition products, both products with a "normal" homologue distribution as well as those with a narrow homologue distribution can be used. The term "normal" homologue distribution refers to mixtures of homologues obtained from the reaction of fatty alcohols and alkylene oxide using alkali metals, alkali metal hydroxides or alkali metal alcoholates as catalysts. Narrow homologue distributions are obtained if, for example, hydrotalcite, alkaline earth metal salts of ether carboxylic acids, alkaline earth metal oxides, hydroxides or alcoholates are used as catalysts. Use of products with a narrow homologue distribution can be preferred.

Agents according to the invention preferably have as the surfactant at least one addition product of 15 to 100 moles ethylene oxide, especially 15 to 50 moles ethylene oxide on a linear or branched (especially linear) fatty alcohol containing 8 to 22 carbon atoms. These are quite particularly preferably—Ceteareth-15, Ceteareth-25 or Ceteareth-50—marketed as Eumulgin® CS 15 (COGNIS), Cremophor A25 (BASF SE) or Eumulgin® CS 50 (COGNIS).

Suitable anionic surfactants include all anionic surface-active materials suitable for use on the human body. They have a water solubilising anionic group, such as a carboxylate, sulfate, sulfonate or phosphate group, and a lipophilic alkyl group containing about 8 to 30 carbon atoms. Additionally, the molecule can have glycol or polyglycol ether groups, ester, ether and amide groups as well as hydroxyl groups. Exemplary suitable anionic surfactants are, each in the form of the sodium, potassium and ammonium, as well as the mono, di and trialkanolammonium salts containing 2 to 4 carbon atoms in the alkanol group.

Examples of suitable anionic surfactants, each in the form of the sodium, potassium and ammonium salts as well as the mono-, di- and trialkanolammonium salts with 2 to 4 carbon atoms in the alkanol group, are
- linear and branched fatty acids with 8 to 30 carbon atoms (soaps),
- ether carboxylic acids of the formula R—O—($CH_2CH_2O$)$_x$—$CH_2$—COOH, wherein R is a linear alkyl group containing 8 to 30 carbon atoms and x=0 or 1 to 16,
- acyl sarcosides with 8 to 24 carbon atoms in the acyl group,
- acyl taurides with 8 to 24 carbon atoms in the acyl group,
- acyl isethionates with 8 to 24 carbon atoms in the acyl group,
- mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups,
- linear alkane sulfonates containing 8 to 24 carbon atoms,
- linear alpha-olefin sulfonates containing 8 to 24 carbon atoms,
- alpha-sulfo fatty acid methyl esters of fatty acids containing 8 to 30 carbon atoms,
- alkyl sulfates and alkyl polyglycol ether sulfates of the Formula R—O($CH_2$—$CH_2O$)$_x$—$OSO_3H$, wherein R is preferably a linear alkyl group containing 8 to 30 carbon atoms and x=0 or 1 to 12,
- mixtures of surface active hydroxyl sulfonates, sulfated hydroxyalkyl polyethylene glycol ethers and/or hydroxyalkylene propylene glycol ethers,
- sulfonated unsaturated fatty acids with 8 to 24 carbon atoms and 1 to 6 double bonds,
- esters of tartaric acid and citric acid with alcohols, which represent the addition products of about 2-15 molecules of ethylene oxide and/or propylene oxide on fatty alcohols containing 8 to 22 carbon atoms,
- alkyl and/or alkenyl ether phosphates of Formula (E1-I),

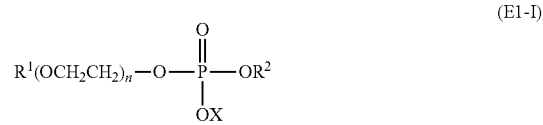

(E1-I)

wherein $R^1$ preferably is an aliphatic hydrocarbon group containing 8 to 30 carbon atoms, $R^2$ is hydrogen, a ($CH^2CH^2O$)$_n R^1$ group or X, n is a number from 1 to 10 and X is hydrogen, an alkali or alkaline earth metal or $NR^3R^4R^5R^6$, with $R^3$ to $R^6$, independently of each other standing for a $C_1$ to $C_4$ hydrocarbon group,
- sulfated fatty acid alkylene glycol esters of the formula (E1-II)

(E1-II)

wherein $R^7CO$— is a linear or branched, aliphatic, saturated and/or unsaturated acyl group with 6 to 22 carbon atoms, Alk is $CH_2CH_2$, $CHCH_3CH_2$ and/or $CH_2CHCH_3$, n is a number from 0.5 to 5, and M is a cation, as described in DE-OS 197 36 906,
- monoglyceride sulfates and monoglyceride ether sulfates of Formula (E1-III)

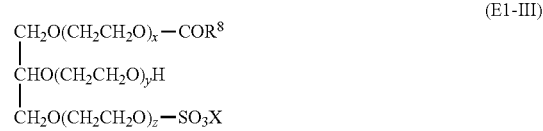

(E1-III)

wherein $R^8CO$ is a linear or branched acyl group containing 6 to 22 carbon atoms, the sum of x, y and z is 0 or a number from 1 to 30, preferably 2 to 10, and X is an alkali metal or alkaline earth metal. In the context of the invention, typical examples of suitable monoglyceride (ether) sulfates are the reaction products of lauric acid monoglyceride, cocoa fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Preferably, monoglyceride sulfates of Formula (E1-III) are employed, wherein $R^8CO$ is a linear acyl group containing 8 to 18 carbon atoms,
- amido ether carboxylic acids,
- condensation products of $C_8$-$C_{30}$ fatty alcohols with protein hydrolyzates and/or amino acids and their derivatives, known to one skilled in the art as albumin fatty acid condensates, such as the Lamepon® types, Gluadin® types, Hostapon® KCG or the Amisoft® types.

Preferred anionic surfactants are alkyl sulfates, alkyl polyglycol ether sulfates and ether carboxylic acids with 10 to 18 C atoms in the alkyl group and up to 12 glycol ether groups in the molecule, sulfosuccinic acid mono and dialkyl esters with 8 to 18 C atoms in the alkyl group and sulfosuccinic acid mono-alkyl polyoxyethyl esters with 8 to 18 C atoms in the alkyl group and 1 to 6 oxyethylene groups, monoglycerin disulfates, alkyl and alkenyl ether phosphates as well as albumin fatty acid condensates.

According to the invention, cationic surfactants of quaternary ammonium compounds, esterquats, and amido amines can likewise be used. Preferred quaternary ammonium compounds are ammonium halides, especially chlorides and bromides, such as alkyl-trimethylammonium chlorides, dialkyldimethylammonium chlorides and trialkylmethylammonium chlorides. The long alkyl chains of these surfactants preferably have 10 to 18 carbon atoms, such as cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Further preferred cationic surfactants are those imidazolium compounds known under the INCI names Quaternium-27 and Quaternium-83.

Zwitterionic surfactants are those surface-active compounds having at least one quaternary ammonium group and at least one —COO or —$SO_3^{(-)}$ group in the molecule. Particularly preferred suitable zwitterionic surfactants are betaines such the N-alkyl-N,N-dimethylammonium glycinates, for example, cocoalkyl-dimethylammonium glycinate, N-acyl-aminopropyl-N,N-dimethylammonium glycinate, for example, coco-acylaminopropyl-dimethylammonium glycinate, and 2-alkyl-3-carboxymethyl-3-hydroxyethyl-imidazolines, each with 8 to 18 carbon atoms in the alkyl or acyl group as well as cocoacyl-aminoethylhydroxyethylcarboxymethyl glycinate. A preferred zwitterionic surfactant is the fatty acid amide derivative known under the INCI name Cocamidopropyl Betaine.

Ampholytes include such surface-active compounds that, apart from a $C_{8-24}$ alkyl or acyl group, have at least one free amino group and at least one —COOH or —$SO_3H$ group in the molecule, and are able to form internal salts. Examples of suitable ampholytes are N-alkylglycines, N-alkyl propionic acids, N-alkylamino butyric acids, N-alkylimino dipropionic acids, N-hydroxyethyl-N-alkylamidopropylglycines, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, cocoacylaminoethylamino propionate and $C_{12}$-$C_{18}$ acyl sarcosine.

Agents according to the invention contain the ingredients or active substances in a cosmetically acceptable carrier.

Preferred cosmetically acceptable carriers are aqueous, alcoholic or aqueous alcoholic media containing preferably at least 10 wt. % water, based on total composition. In particular, lower alcohols containing 1 to 4 carbon atoms, such as ethanol and isopropanol, which are usually used for cosmetic purposes, can be used as alcohols. It is inventively preferred to incorporate at least one ($C_1$ to $C_4$) monoalkyl alcohol in the agents, particularly in an amount of 1 to 50 wt. %, especially 5 to 30 wt. %. Again, this is particularly preferred when manufacturing pump foams or aerosol foams.

Organic solvents or a mixture of solvents with a boiling point of less than 400° C. can be uase as additional co-solvents in an amount of 0.1 to 15 wt. %, preferably 1 to 10 wt. %, based on total weight of the agent. Particularly suitable additional co-solvents are unbranched or branched hydrocarbons such as pentane, hexane, isopentane, and cyclic hydrocarbons such as cyclopentane and cyclohexane. Additional, particularly preferred water-soluble solvents are glycerin, ethylene glycol and propylene glycol in an amount of up to 30 wt. %, based on total weight of the agent.

In particular, the addition of glycerin and/or propylene glycol and/or polyethylene glycol and/or polypropylene glycol increases the flexibility of the polymer film formed when the agent is used. Consequently, if a more flexible hold is desired, then the agents preferably contain 0.01 to 30 wt. % glycerin and/or propylene glycol and/or polyethylene glycol and/or polypropylene glycol, based on total weight of the agent.

The agents preferably have a pH of 2 to 11. The pH range is particularly preferably from 2 to 8. In the context of this publication, pH data refer to the pH at 25° C. unless otherwise stated.

Agents according to the invention can also include auxiliaries and additives typically used in styling agents.

In particular, care products may be mentioned as suitable auxiliaries and additives.

Silicone oil and/or silicone gum, for example, can be used as the care substance.

Suitable silicone oils or gums according to the invention are especially dialkyl and alkylarylsiloxanes, such as dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils afford a variety of effects. Thus, for example, they simultaneously influence dry and wet combability, feel of the dry and wet hair, as well as gloss. The term "silicone oils" refers to organosilicon compounds having a plurality of structures. In the first instance they include the Dimethiconols. The following commercial products are exemplary of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzene sulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all from Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all from Dow Corning Corporation), Dub Gel SI 1400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), San-Surf Petrolatum-25, Satin Finish (both from Collaborative Laboratories, Inc.), Silatex-D30 (Cosmetic Ingredient Resources), Silsoft 148, Silsoft E-50, Silsoft E-623 (all from Crompton Corporation), SM555, SM2725, SM2765, SM2785 (all from GE Silicones), Taylor T-Sil CD-1, Taylor TME-4050E (all from Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

Dimethicones form the second group of the silicones that can be used according to the invention. They can be linear, branched, cyclic, or cyclic and branched.

Dimethicone copolyols (S3) form a further group of suitable silicones. Suitable Dimethicone copolyols are commercially available and marketed, for example, by Dow Corning under the trade name Dow Corning® 5330 Fluid.

Naturally, the Dimethiconols, Dimethicones and/or Dimethicone copolymers can already be present as an emulsion. Corresponding emulsions of the Dimethiconols, Dimethicones and/or Dimethicone copolymers can be produced both after the production of the corresponding Dimethiconols, Dimethicones and/or Dimethicone copolymers from these and the usual emulsification processes known to one skilled in the art. Cationic, anionic, non-ionic or zwitterionic surfactants and emulsifiers can be used as auxiliaries and adjuvants for production of the corresponding emulsions. Naturally, the emulsions of Dimethiconols. Dimethicones and/or Dimethicone copolymers can also be produced directly by emulsion polymerization process. These types of processes are also well known to the person skilled in the art.

When the Dimethiconols, Dimethicones and/or Dimethicone copolymers are used as an emulsion, then the droplet size of the emulsified particles ranges from 0.01 to 10,000 µm, preferably 0.01 to 100 µm, particularly preferably 0.01 to 20 µm and quite particularly preferably 0.01 to 10 µm. Particle size is determined here according to the light scattering method.

If branched Dimethiconols, Dimethicones and/or Dimethicone copolymers are used, then the branching is greater than a fortuitous branching that accidentally occurs from impurities in the respective monomers. Accordingly, in the context of the present invention, the degree of branching is understood to be greater than 0.01% for branched Dimethiconols, Dimethicones and/or Dimethicone copolymers. The degree of branching is preferably greater than 0.01% and quite particularly preferably greater than 0.5%. The degree of branching is determined from the ratio of unbranched monomers to branched monomers (i.e., the amount of tri- and tetrafunctional siloxanes). According to the invention, both low-branched and highly branched Dimethiconols, Dimethicones and/or Dimethicone copolymers can be quite particularly preferred.

Further suitable silicones are amino-functional silicones, especially silicones compiled under the INCI name Amodimethicone. Consequently, it is inventively preferred when the agents additionally have at least one amino-functional silicone. These are silicones having at least one, optionally substituted, amino group. These silicones are designated as Amodimethicones according to INCI nomenclature and are available, for example, in the form of an emulsion as the commercial product Dow Corning® 939 or as the commercial product Dow Corning® 949 in a mixture with a cationic and a non-ionic surfactant.

Preferably, those amino functional silicones are used which have an amine number of 0.25 meq/g or greater, preferably 0.3 meq/g or greater, and particularly preferably 0.4 meq/g or greater. The amine number is the milli-equivalents of amine per gram of amino functional silicone. It can be measured by titration and can also be reported with the unit mg KOH/g.

The agents preferably contain the silicones in amounts of 0.01 wt. % to 15 wt. %, particularly preferably in amounts of 0.05 to 2 wt. %, based on total weight of the agent.

The composition can include, for example, at least one protein hydrolysate and/or one of its derivatives as a care substance of another compound class.

Protein hydrolysates are product mixtures obtained by acid-, base- or enzyme-catalyzed degradation of proteins (albumins). According to the invention, the term "protein hydrolysates" refers to total hydrolysates as well as individual amino acids and their derivatives as well as mixtures of different amino acids. The molecular weight of the protein hydrolyzates utilizable according to the invention ranges from 75, the molecular weight of glycine, to 200,000, preferably the molecular weight is 75 to 50,000 and quite particularly preferably 75 to 20,000 Dalton.

According to the invention, the added protein hydrolysates can be of vegetal as well as animal or marine or synthetic origin.

Animal protein hydrolyzates are, for example, elastin, collagen, keratin, silk protein, and milk albumin protein hydrolyzates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

The agents contain protein hydrolyzates, for example, in concentrations of 0.01 wt. % to 20 wt. %, preferably 0.05 wt. % up to 15 wt. % and quite particularly preferably in amounts of 0.05 wt. % up to 5 wt. %, based on total weight of the end-use preparation.

The agent can further contain at least one vitamin, one provitamin, one vitamin precursor and/or one of their derivatives as the care substance.

According to the invention, such vitamins, provitamins and vitamin precursors are preferred that are normally classified in the groups A, B, C, E, F and H.

The group of substances designated as vitamin A includes retinol (vitamin A1) as well as 3,4-didehydroretinol (vitamin A2). β-Carotene is the provitamin of retinol. Examples of suitable vitamin A components according to the invention are vitamin A acid and its esters, vitamin A aldehyde and vitamin A alcohol as well as its esters such as the palmitate and acetate. The agents preferably comprise the vitamin A components in amounts of 0.05 to 1 wt. %, based on the total application preparation.

The vitamin B group or the vitamin B complex include inter alia vitamin B1 (thiamine), vitamin B2 (riboflavin), vitamin B3 (nicotinic acid and/or nicotinic acid amide (niacinamide)), vitamin B5 (pantothenic acid, panthenol and pantolactone), vitamin B6 (pyridoxine as well as pyridoxamine and pyridoxal), vitamin C (ascorbic acid), vitamin E (tocopherols, especially α-tocopherol), vitamin F (linoleic acid and/or linolenic acid), vitamin H.

The agents preferably contain vitamins, provitamins and vitamin precursors from groups A, B, C, E and H. Panthenol, pantolactone, pyridoxine and its derivatives as well as nicotinamide and biotin are especially preferred.

D-panthenol is quite particularly preferably employed as a care substance, optionally in combination with at least one of the abovementioned silicone derivatives.

Like the addition of glycerin and/or propylene glycol, the addition of panthenol increases the flexibility of the polymer film formed when the agent is used. Thus, if a particularly flexible hold is desired, then the agents can contain panthenol instead of or in addition to glycerin and/or propylene glycol. In a preferred embodiment, the agents contain panthenol, preferably in an amount of 0.05 to 10 wt. %, particularly preferably 0.1 to 5 wt. %, based on total weight of the agent.

Agents according to the invention can further contain at least one plant extract as a care substance.

Usually, these extracts are manufactured by extraction of the whole plant. In individual cases, however, it can also be preferred to produce the extracts solely from blossoms and/or leaves of the plant.

According to the invention, extracts mainly from green tea, oak bark, stinging nettle, hamamelis, hops, henna, chamomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, rest-h, rest-harrow, coltsfoot, marshmallow (althea), meristem, ginseng and ginger are preferred.

In addition, it can be preferred to use mixtures of a plurality, particularly two different plant extracts in agents according to the invention.

Mono- or oligosaccharides can also be used as care substance in agents according to the invention.

Monosaccharides as well as oligosaccharides, such as raw sugar, lactose and raffinose, can be used. According to the invention, use of monosaccharides is preferred. Once again, the monosaccharides preferably include those compounds having 5 or 6 carbon atoms.

Suitable pentoses and hexoses are, for example, ribose, arabinose, xylose, lyxose, allose, altrose, glucose, mannose, gulose, idose, galactose, talose, fucose and fructose.

Arabinose, glucose, galactose and fructose are the preferably used carbohydrates; glucose is quite particularly preferably incorporated, and is suitable both in the D(+) or L(−) configuration or as the racemate.

In addition, derivatives of these pentoses and hexoses can also be incorporated according to the invention, such as the corresponding onic and uronic acids (sugar acids), sugar alcohols, and glycosides.

Preferred sugar acids are the gluconic acid, the glucuronic acid, the sugar acids, the mannosugar acids and the mucic acids. Preferred sugar alcohols are sorbitol, mannitol and dulcitol.

Preferred glycosides are the methyl glucosides.

As the incorporated mono- and oligosaccharides are usually obtained from natural raw materials such as starch, they generally possess configurations that correspond to these raw materials (e.g., D-glucose, D-fructose and D-galactose).

The inventive agents preferably contain mono- or oligosaccharides in an amount of 0.1 to 8 wt. %, particularly preferably 1 to 5 wt. %, based on total end-use preparation.

The agent can further comprise at least one lipid as a care substance.

According to the invention, suitable lipids are phospholipids, for example, soy lecithin, egg lecithin and cephalins, as well as substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are commercialized, for example, by the Mona Company under the trade names Phospholipid EFA®, Phospholipid PTC® and Phospholipid SV®. The agents preferably include the lipids in amounts of 0.01 to 10 wt. %, particularly 0.1 to 5 wt. %, based on total end-use preparation.

Oil bodies are also suitable as a care substance.

Natural and synthetic cosmetic oil bodies include, for example:

vegetal oils. Examples of such oils are sunflower oil, olive oil, soya oil, rapeseed oil, almond oil, jojoba oil, orange oil, wheat germ oil, peach stone oil and the liquid parts of coconut oil. However, other triglyceride oils such as the liquid fractions of beef tallow are also suitable as well as synthetic triglyceride oils, liquid paraffin oils, isoparaffin oils and synthetic hydrocarbons, as well as di-n-alkyl ethers containing a total of 12 to 36 carbon atoms, particularly 12 to 24 carbon atoms such as di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert.butyl ether, diisopentyl ether, di-3-ethyldecyl ether, tert.butyl n-octyl ether, isopentyl n-octyl ether and 2-methylpentyl n-octyl ether. The commercial products of the compounds 1,3-di-(2-ethylhexyl)cyclohexane (Cetiol® S) and di-n-octyl ether (Cetiol® OE) can be preferred.

Ester oils. Ester oils refer to the esters of $C_6$-$C_{30}$ fatty acids with $C_2$-$C_{30}$ fatty alcohols. The monoesters of fatty acids with alcohols containing 2 to 24 carbon atoms are preferred. According to the invention, isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerin tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

dicarboxylic acid esters such as di-n-butyl adipate, di-(2-ethylhexyl) adipate, di-(2-ethylhexyl) succinate and di-isotridecyl acetate as well as diol esters such as ethylene glycol dioleate, ethylene glycol di-isotridecanoate, propylene glycol di(2-ethylhexanoate), propylene glycol di-isostearate, propylene glycol di-pelargonate, butane diol di-isostearate, neopentyl glycol dicaprylate, symmetrical, unsymmetrical or cyclic esters of carbon dioxide with fatty alcohols, such as described in DE-OS 197 56 454, glycerin carbonate or dicaprylyl carbonate (Cetiol® CC), trifatty acid esters of saturated and/or unsaturated linear and/or branched fatty acids with glycerin, fatty acid partial glycerides, under which are understood monoglycerides, diglycerides and their industrial mixtures. When using industrial products, minor amounts of triglycerides may still be contained as a result of the production process. The partial glycerides preferably comply with the Formula (D4-I),

(D4-I)

wherein $R^1$, $R^2$ and $R^3$ are, independently of each other, hydrogen or a linear or branched, saturated and/or unsaturated acyl group with 6 to 22 carbon atoms, preferably 12 to 18 carbon atoms, with the proviso that at least one of these groups is an acyl group and at least one of these groups is hydrogen. The sum of (m+n+q) is 0 or a number from 1 to 100, preferably 0 or 5 to 25. Preferably, $R^1$ is an acyl group and $R^2$ and $R^3$ are hydrogen and the sum of (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The added amount of natural and synthetic cosmetic oil bodies in agents according to the invention is usually 0.1 to 30 wt. %, based on total end-use preparation, preferably 0.1 to 20 wt. % and particularly 0.1 to 15 wt. %.

Although each of the cited care substances alone already provides a satisfactory result, in the context of the present invention all embodiments are also included, wherein the agent has a plurality of conditioners even from different groups.

By addition of a UV filter, both the agent itself as well as the treated fibers can be protected against damage from UV radiation. Consequently, at least one UV filter is preferably added to the agent. Suitable UV filters are generally not limited with respect to their structure and physical properties. Indeed, all UV filters that can be used in the cosmetic field having an absorption maximum in the UVA (315-400 nm), UVB (280-315 nm) or UVC (<280 nm) regions are suitable. UV filters having an absorption maximum in the UVB region, especially in the range from about 280 to about 300 nm, are particularly preferred.

Preferred UV-filters are chosen from substituted benzophenones, p-aminobenzoates, diphenylacrylates, cinnamates, salicylates, benzimidazoles and o-aminobenzoates.

Exemplary inventively usable UV-filters are 4-amino-benzoic acid, N,N,N-trimethyl-4-(2-oxoborn-3-ylidenemethyl) aniline methyl sulfate, 3,3,5-trimethylcyclohexyl salicylate (Homosalate), 2-hydroxy-4-methoxy-benzophenone (Benzophenone-3; Uvinul®M 40, Uvasorb® MET, Neo Heliopan® BB, Eusolex® 4360), 2-phenylbenzimidazol-5-sulfonic acid and their potassium, sodium und triethanolamine salts (phenylbenzimidazole sulfonic acid; Parsol® HS; Neo Heliopan® Hydro), 3,3'-(1,4-phenylenedimethylene)-bis(7,7-dimethyl-2-oxo-bicyclo-[2.2.1]hept-1-yl-methanesulfonic acid) and their salts, 1-(4-tert.-butylphenyl)-3-(4-methoxyphenyl)propane-1,3-dione (butylmethoxydibenzoylmethane; Parsol® 1789, Eusolex® 9020), α-(2-oxoborn-3-ylidene)-toluene-4-sulfonic acid and salts thereof, ethoxylated ethyl 4-aminobenzoate (PEG-25 PABA; Uvinul® P 25), 2-ethylhexyl 4-dimethylaminobenzoate (Octyl Dimethyl PABA; Uvasorb® DMO, Escalol® 507, Eusolex® 6007), 2-ethylhexyl salicylate (Octyl Salicylate; Escalol® 587, Neo Heliopan® OS, Uvinul® O18), isopentyl 4-methoxycinnamate (isoamyl p-methoxycinnamate; Neo Heliopan®E 1000), 2-ethylhexyl 4-methoxycinnamate (Octyl Methoxycinnamate; Parsol® MCX, Escalol® 557, Neo Heliopan® AV), 2-hydroxy-4-methoxybenzophenone-5-sulfonic acid and sodium salts thereof, (benzophenone-4; Uvinul® MS 40; Uvasorb® S 5), 3-(4'-methylbenzylidene)-D,L-camphor (4-methylbenzylidene camphor; Parsol® 5000, Eusolex® 6300), 3-benzylidene-camphor (3-Benzylidene camphor), 4-isopropylbenzyl salicylate, 2,4,6-tri-anilino-(p-carbo-2'-ethylhexyl-1'-oxy)-1,3,5-triazine, 3-imidazol-4-yl-acrylic acid and its ethyl ester, polymers of N-{(2 and 4)-[2-oxoborn-3-ylidenemethyl]benzyl}-acrylamide, 2,4-dihydroxybenzophenone (Benzophenone-1; Uvasorb® 20 H, Uvinul® 400), 2-ethylhexyl ester of 1,1'-diphenylacrylonitrilic acid (Octocrylene; Eusolex® OCR, Neo Heliopan® Type 303, Uvinul® N 539 SG), menthyl o-aminobenzoate (menthyl anthranilate; Neo Heliopan® MA), 2,2',4,4'-tetrahydroxybenzophenone (Benzophenone-2, Uvinul® D-50), 2,2'-dihydroxy-4,4'-dimethoxybenzophenone (Benzophenone-6), sodium 2,2'-dihydroxy-4,4'-dimethoxybenzophenone-5-sulfonate and 2'-ethylhexyl 2-cyano-3,3-diphenylacrylate. 4-Amino-benzoic acid, N,N,N-trimethyl-4-(2-oxoborn-3-ylidenemethyl)aniline methyl sulfate, 3,3,5-trimethyl-cyclohexyl salicylate, 2-hydroxy-4-methoxybenzophenone, 2-phenylbenzimidazole-5-sulfonic acid and the potassium, sodium and triethanolamine salts thereof, 3,3'-(1,4-phenylenedimethylene)-bis(7,7-dimethyl-2-oxo-bicyclo-[2.2.1]hept-1-yl methane sulfonic acid) and salts thereof, 1-(4-tert.-butylphenyl)-3-(4-methoxyphenyl)-propane-1,3-dione, α-(2-oxoborn-3-ylidene)-toluene-4-sulfonic acid and salts thereof, ethoxylated ethyl 4-aminobenzoate, 2-ethylhexyl 4-dimethylaminobenzoate, 2-ethylhexyl salicylate, isopentyl 4-methoxycinnamate, 2-ethylhexyl 4-methoxycinnamate, 2-hydroxy-4-methoxybenzophenone-5-sulfonic acid and its sodium salt, 3-(4'-methylbenzylidene)-D,L-camphor, 3-benzylidene-camphor, 4-isopropylbenzyl salicylate, 2,4,6-tri-anilino-(p-carbo-2'-ethylhexyl-1'-oxy)-1,3,5-triazine, 3-imidazol-4-yl-acrylic acid and its ethyl ester, polymers of N-{(2 and 4)-[2-oxoborn-3-ylidenemethyl]benzyl}acrylamide are preferred. According to the invention, 2-hydroxy-4-methoxy-benzophenone, 2-phenylbenzimidazole-5-sulfonic acid and its potassium, sodium and triethanolamine salts, 1-(4-tert.-butylphenyl)-3-(4-methoxyphenyl)-propane-1,3-dione, 4-methoxycinnamic acid 2-ethylhexyl ester and 3-(4'-methylbenzylidene)-D,L-camphor are quite particularly preferred.

The agent usually contains UV filters in amounts of 0.01 to 5 wt. %, based on total end-use preparation. Quantities of 0.1-2.5 wt. % are preferred.

In a particular embodiment, the agent further includes one or more substantive dyes. Application of the agent then enables the treated keratinic fiber not only to be temporarily styled but also to be dyed at the same time. This can be particularly desirable when only a temporary dyeing is desired, for example with flamboyant fashion colors that can be subsequently removed from the keratinic fibers by simply washing them out.

Substantive dyes are usually nitrophenylenediamines, nitroamino phenols, azo dyes, anthraquinones or indophenols. Preferred substantive dyestuffs are the compounds known under the international designations or trade names HC Yellow 2, HC Yellow 4, HC Yellow 5, HC Yellow 6, HC Yellow12, Acid Yellow 1, Acid Yellow 10, Acid Yellow 23, Acid Yellow 36, HC Orange 1, Disperse Orange 3, Acid Orange 7, HC Red 1, HG Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 known compounds as well as 1,4-diamino-2-nitrobenzene, 2-amino-4-nitrophenol, 1,4-bis(β-hydroxyethyl)amino-2-nitrobenzene, 3-nitro-4(β-hydroxyethyl)aminophenol, 2-(2'-hydroxyethyl)amino-4-6-dinitrophenol, 1-(2'-hydroxyethyl)amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene. Cationic substantive dyes are preferably employed. Particular preference is given here to (a) cationic triphenylmethane dyes, such as Basic Blue 7, Basic Blue 26, Basic Violet 2 and Basic Violet 14,
(b) aromatic systems substituted by a quaternary nitrogen group, such as Basic Yellow 57, Basic Red 76, Basic Blue 99, Basic Brown 16 and Basic Brown 17, and
(c) substantive dyes having a heterocycle that has at least one quaternary nitrogen atom, as specified, for example, in EP-A2-998 908 in claims 6 to 11.

The dyes which are also known under the names Basic Yellow 87, Basic Orange 31 and Basic Red 51 are quite particularly preferred cationic substantive dyes of group (c). The cationic substantive dyes that are commercialized under the trade name Arianor® are likewise quite particularly preferred cationic substantive dyes according to the invention.

Inventive agents according to this embodiment contain substantive dyes preferably in an amount of 0.001 to 20 wt. %, based on total agent.

Preferably, the agents are exempt from oxidation dye precursors. Oxidation dye precursors are divided into developer components and coupler components. Under the influence of oxidizing agents or from atmospheric oxygen, the developer components form the actual colorants among each other or by coupling with one or more coupler components.

Formulation of the agents can be in all forms typical for styling agents, for example, in the form of solutions that can be applied as hair water or pump or aerosol spray onto the hair, in the form of creams, emulsions, waxes, gels or also surfactant-containing foaming solutions or other preparations suitable for application on the hair.

Hair creams and hair gels generally include structurants and/or thickening polymers which give the desired consistency to the products. Structurants and/or thickening polymers are typically added in amounts of 0.1 to 10 wt. %, based on total product. Quantities of 0.5 to 5 wt. %, particularly 0.5 to 3 wt. %, are preferred.

The agents are preferably packed as a pump spray, aerosol spray, pump foam or aerosol foam.

For this, the agents are packed in a dispensing device, illustrated by either a pressurized gas container additionally containing a propellant ("aerosol container"), or by a non-aerosol container.

Pressurized gas containers, by which a product is dispersed through a valve by the internal gas pressure in the container, are defined as "aerosol containers". The opposite of the aerosol definition, a container under normal pressure, is defined as a "non-aerosol container", from which a product is dispersed by means of the mechanical actuation of a pump system.

Agents according to the invention are preferably packed as an aerosol hair foam or aerosol hair spray. Consequently, the agent additionally has at least one propellant.

Suitable exemplary propellants are chosen from $N_2O$, dimethyl ether, $CO_2$, air, alkanes containing 3 to 5 carbon atoms, such as propane, n-butane, iso-butane, n-pentane and iso-pentane, and their mixtures. Dimethyl ether, propane, n-butane, iso-butane and their mixtures are preferred.

According to a preferred embodiment, the cited alkanes, mixtures of the cited alkanes or mixtures of the cited alkanes with dimethyl ether are preferred as the sole propellant. However, the invention also includes joint utilization with propellants of the fluorochlorohydrocarbon type, especially fluorinated hydrocarbons.

With respect to the weight ratio of propellant to the usual ingredients of the preparation, the size of the aerosol droplets or the foam bubbles and the relevant size distribution can be adjusted for a given spray device.

The amount of added propellant varies as a function of the actual composition of the agent, packaging used and the desired product type, for example, hair spray or hair foam. When a conventional spray device is used, aerosol foam products preferably contain propellant in amounts of 1 to 35 wt. %, based on total product. Quantities of 2 to 30 wt. %, especially 3 to 15 wt. %, are particularly preferred. Aerosol sprays generally contain greater amounts of propellant. Here, the propellant is preferably added in amounts of 30 to 98 wt. %, based on total product. Quantities of 40 to 95 wt. %, especially 50 to 95 wt. %, are particularly preferred.

The aerosol products can be manufactured according to conventional techniques. Generally, all ingredients of the agent except the propellant are charged into a suitable pressure-resistant container. This is then sealed with a valve. The desired quantity of propellant is then filled by conventional techniques.

Agents in the form of gels are foamed in a two-chamber aerosol container, preferably with isopentane as the propellant, which added to the agent and packed in the first chamber of the two-chamber aerosol container. At least one additional propellant different from isopentane is packed in the second chamber of the two-chamber aerosol container and generates a higher pressure than the isopentane. Propellants of the second chamber are preferably chosen from $N_2O$, dimethyl ether, $CO_2$, air, alkanes containing 3 or 4 carbon atoms (such as propane, n-butane, iso-butane) as well as mixtures thereof.

Aerosol hair foams or aerosol hair sprays containing the above described agent according to the invention and at least one propellant are a preferred embodiment of the agent.

Preferred agents according to the invention and propellants of the aerosol hair foam or aerosol hair spray, as well as relevant amounts of propellant correspond to those already mentioned above.

A second subject matter of the invention is the use of the agent for temporary shaping of hair and/or for hair care.

The agents and products containing these agents, especially aerosol hair foams or aerosol hair sprays, give the treated hair a very strong, long-lasting hold to the hairstyle, while the hair remains flexible. If the agent is made up as a hair foam, then a stable, micro-porous and creamy foam is formed that can be uniformly dispersed on the hair without dripping.

A third subject matter of the invention is a method for treating keratin-containing fibers, especially human hair, wherein an agent according to the first subject matter is foamed to a foam by use of a dispensing device, and the resulting foam is applied onto the keratin-containing fibers.

It is inventively preferred to shape the keratin-containing fibers and this shape is fixed by the agent of the first subject matter of the invention.

The abovementioned dispensing devices (see above) are inventively preferred.

A fourth subject matter of the invention is a method for treating keratin-containing fibers, especially human hair, wherein an agent according to the first subject matter is applied as a spray onto the keratin-containing fibers by a dispensing device.

It is inventively preferred here that the keratin-containing fibers are shaped and this shape is fixed by the agent of the first subject matter of the invention.

The abovementioned dispensing devices (see above) are inventively preferred.

The following examples are intended to illustrate the subject matter of the present invention in more detail, without limiting it in any way.

EXAMPLES

Unless otherwise stated, the quantities are understood to be in weight percent.

The following formulations were prepared by blending the raw materials:

| Raw materials | A | B | C | D | E |
|---|---|---|---|---|---|
| Luviquat ® Supreme | 9.0 | — | 5.0 | 3.0 | — |
| Luviquat ® FC 370 | — | 4.0 | — | 5.0 | 7.0 |
| Aquastyle ® 300 | 3 | 2.0 | 1.0 | 4.0 | 3.5 |
| Styleze ® W-10 | — | 3.0 | — | — | — |
| Styleze ® W-20 | — | — | 2.0 | — | — |
| PEG-40 hydrogenated castor oil | 0.1 | 0.2 | 0.2 | 0.2 | 0.1 |
| Water | ←--------ad 100--------→ | | | | |

| Raw materials | F | G | H | I | J | K |
|---|---|---|---|---|---|---|
| Aquastyle ® 300 | 4.0 | 2.0 | 5.0 | 2.0 | 4.0 | 4.0 |
| Celquat ® L-200 | 1.0 | 1.0 | 0.5 | — | — | 1.0 |
| Luviquat ® Supreme | — | — | — | — | 4.0 | — |
| Luviquat ® FC 370 | — | — | 4.0 | — | — | — |
| Styleze ® W-10 | 6.0– | 2.0 | — | 4.0 | — | — |
| Styleze ® W-20 | — | — | — | — | — | 4.0 |
| Gafquat ® 755 N PW | — | — | — | 6.0 | 3.0 | — |
| Styleze ® CC 10 | — | 2.0 | — | — | — | — |
| Ethanol | 15.0 | — | — | — | — | 15.0 |
| PEG-40 hydrogenated castor oil | 0.1 | 0.1 | 0.15 | 0.2 | 0.2 | 0.1 |
| Water | ←--------ad 100--------→ | | | | | |

Formulations A to K were each filled into an aerosol container that meets the following technical parameter: aluminium reservoir container with valve product 522983 PV 10697 from the Precision Company (Deutsche Präzisions-Ventil GmbH).

The aerosol container was filled with a mixture of the propellant gases propane/butane (47 wt. % propane, 50 wt. % butane, 3 wt. % isobutene), such that the weight ratio of the formulation to the propellant gas was 92 to 8.

All formulations when applied onto the hair produced an outstandingly flexible hold to the hairstyle. The hair received a very good care. When the formulations were deployed as aerosol foam, voluminous foam was obtained that broke down when applied on the hair.

Index of the raw materials:

Aquastyle® 300 copolymer of N-vinyl pyrrolidone/N-vinyl caprolactam/N-(3-dimethylaminopropyl)methacrylamide and 3-(methacryloylamino)propyl-lauryl-dimethylammonium chloride (active substance 30 wt % in water/ethanol, INCI name: (Polyquaternium-69) (ISP)

Celquat® L 200 quaternized cellulose derivative (INCI name: Polyquaternium-4) (National Starch)

Gafquat® 755 N PW dimethylaminoethyl methacrylate-vinyl pyrrolidone copolymer, quaternized with diethyl sulfate (ca. 19% solids in water; INCI name: Polyquaternium-11) (ISP)

Luviquat® FC 370 3-methyl-1-vinylimidazolium chloride-vinyl pyrrolidone copolymer (30:70) (38-42% solids in water; INCI name: Polyquaternium-16) (BASF)

Luviquat® Supreme vinyl pyrrolidone-methacrylamide-vinylimidazole-vinylimidazolium methosulfate copolymer (55:29:10:6) (19-21% solids in water; INCI name: Polyquaternium-68) (BASF)

Styleze® W-10 copolymer of N-vinyl pyrrolidone, N,N-dimethylaminopropylmethacrylamide and N,N-dimethyl-N-dodecylammoniopropylmethacrylamide chloride (ca. 9 to 11% active substance, INCI name: Polyquaternium-55) (ISP)

Styleze® W-20 copolymer of N-vinyl pyrrolidone, N,N-dimethylaminopropylmethacrylamide and N,N-dimethyl-N-dodecylammoniopropylmethacrylamide chloride (ca. 19 to 21% active substance, INCI name: Polyquaternium-55) (ISP)

Styleze® CC 10 copolymer of N-vinyl pyrrolidone and N,N-dimethylaminopropylmethacrylamide (ca. 9 to 11% active substance, INCI name: VP/DMAPA Acrylates Copolymer) (ISP)

We claim:

1. An agent for treating keratin-containing fibers comprising, in a cosmetically acceptable carrier:
   (a) at least one amphiphilic, cationic polymer having at least one structural unit of Formula (I), at least one structural unit of Formula (II), at least one structural unit of Formula (III) and at least one structural unit of Formula (IV),

(I)

(II)

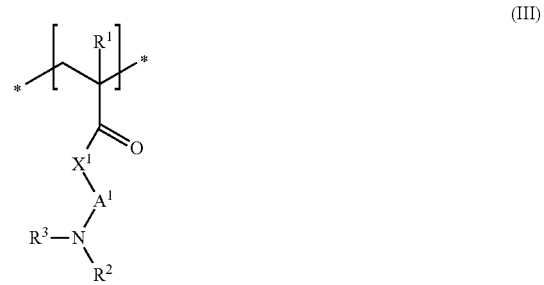

(III)

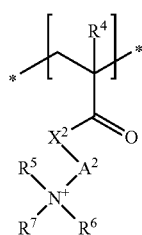
(IV)

wherein
$R^1$ and $R^4$ are, independently of one another, hydrogen atom or a methyl group,
$X^1$ and $X^2$ are, independently of one another, an oxygen atom or an NH group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group, and $R^7$ is a ($C_8$ to $C_{30}$) alkyl group, and
(b) at least one additional film-forming cationic and/or setting cationic polymer having at least one structural unit of Formula (Poly1),

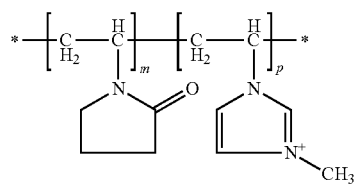
(Poly1)

wherein indices m and p vary according to the molecular mass of the polymer.

2. The agent according to claim 1 wherein in Formula (III) and Formula (IV), $R^1$ and $R^4$ are each a methyl group.

3. The agent according to claim 1 wherein in Formula (III) and Formula (IV), $A^1$ and $A^2$ are, independently of one another, ethane-1,2-diyl or propane-1,3-diyl.

4. The agent according to claim 1 wherein in Formula (III) and Formula (IV), $R^2$, $R^3$, $R^5$ and $R^6$ are, independently of one another, methyl or ethyl.

5. The agent according to claim 1 wherein in Formula (IV) $R^7$ is a ($C_{10}$ to $C_{24}$) alkyl group.

6. The agent according to claim 5 wherein in Formula (IV) $R^7$ is decyl (caprinyl), dodecyl (lauryl), tetradecyl (myristyl), hexadecyl (cetyl), octadecyl (stearyl), eicosyl (arachyl) or docosyl (behenyl).

7. The agent according to claim 1 wherein the amphiphilic, cationic polymer contains at least one structural unit of Formula (I), at least one structural unit of Formula (II), at least one structural unit of Formula (III-8) and at least one structural unit of Formula (IV-8)

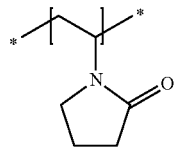
(I)

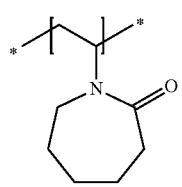
(II)

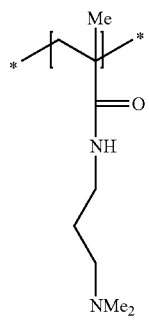
(III-8)

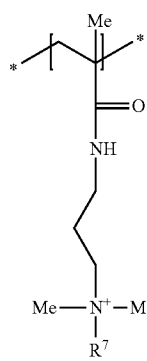
(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl).

8. The agent according to claim 1 wherein the amphiphilic, cationic polymers are present in an amount of 0.1 wt. % to 20.0 wt. %, based on total weight of the agent.

9. The agent according to claim 1 wherein the film-forming cationic and/or setting cationic polymers (b) are present in an amount of 0.1 wt. % to 20.0 wt. %, based on total weight of the agent.

10. The agent according to claim 1, provided in the form of an aerosol foam or aerosol spray comprising the agent according to claim 1.

* * * * *